United States Patent
Fukuda et al.

(10) Patent No.: US 7,449,568 B2
(45) Date of Patent: Nov. 11, 2008

(54) ALGA-ORIGIN PROMOTER, INTRON AND TERMINATOR

(75) Inventors: Satoru Fukuda, Hakodate (JP);
Naotsune Saga, Hakodate (JP);
Toshiharu Ohba, Yokkaichi (JP);
Sawako Nagashima, Otsu (JP); Shuichi Takahashi, Kusatsu (JP); Kiyozo Asada, Shiga (JP); Ikunoshin Kato, Shiga (JP)

(73) Assignee: Takara Bio Inc., Shiga (JP)

( * ) Notice: Subject to any disclaimer, the term of this patent is extended or adjusted under 35 U.S.C. 154(b) by 632 days.

(21) Appl. No.: 10/503,467

(22) PCT Filed: Feb. 26, 2003

(86) PCT No.: PCT/JP03/02112

§ 371 (c)(1),
(2), (4) Date: Aug. 4, 2004

(87) PCT Pub. No.: WO03/072775

PCT Pub. Date: Sep. 4, 2003

(65) Prior Publication Data

US 2006/0234368 A1    Oct. 19, 2006

(30) Foreign Application Priority Data

Feb. 28, 2002 (JP) ............................. 2002-52885
Dec. 25, 2002 (JP) ............................. 2002-374188

(51) Int. Cl.
*C07H 21/04* (2006.01)
*C12N 15/82* (2006.01)
*C12N 5/14* (2006.01)

(52) U.S. Cl. .................... 536/24.1; 435/320.1; 800/278

(58) Field of Classification Search .................. None
See application file for complete search history.

(56) References Cited

OTHER PUBLICATIONS

Hawkins et al. 1999 Current Microbiology 38:335-341.*
Kim et al. 1994, Plant Molecular Biology 24: 105-117.*
Fourgoux-Nicol et al. 1999, Plant Molecular Biology 40 :857-872.*
Fukuda, S. et al "Isolation, characterization and expression of a cDNA encoding an elongation factor-1α from *Porphyra yezoensis* (Bangiales, Rhodophyta)" Phycological Research vol. 50 2002 pp. 11-15.
Kuwano, K. et al "Cryopreservation of clonal gametophytic thalli of *Porphyra* (Rhodophyta)" Plant Science vol. 116 1996 pp. 117-124.
Lee, E.K. et al "Analysis of Expressed Sequence Tags of *Porphyra yezoensis*" Molecules and Cells, vol. 10 No. 3, pp. 338-342.
Liu, Q.Y. et al "Elongation factor 1α genes of the red alga *Porphyra purpurea* Include a novel, developmentally specialized variant" Plant Molecular Biology, vol. 31, 1996 pp. 77-85.
Nikaido, I. et al "Generation of 10,154 Expressed Sequence Tags from a Leafy Gametophyte of a Marine Red Alga, *Porphyra yezoensis*" DNA Research vol. 7 2000 pp. 223-227.
Tanaka, A. et al "Enhancement of foreign gene expression by a dicot intron in rice but not in tobacco is correlated with an increaded level of mRNA and an efficient splicing of the intron" Nucleic Acids Research, vol. 18, No. 23 pp. 6767-6770.

* cited by examiner

*Primary Examiner*—Elizabeth McElwain
*Assistant Examiner*—Li Zheng
(74) *Attorney, Agent, or Firm*—Browdy and Neimark, PLLC

(57) ABSTRACT

A promoter, an intron and a terminator by which a useful foreign gene can be efficiently expressed in algae and which are thus useful in breeding algae using genetic engineering techniques.

6 Claims, 4 Drawing Sheets

ALGA-ORIGIN PROMOTER, INTRON AND TERMINATOR

TECHNICAL FIELD

The present invention relates to a promoter and a vector for gene expression which are used for breeding of algae using genetic engineering techniques and industrial production using algal cells.

BACKGROUND ART

Traditionally, obtainment of an industrially useful alga has relied on collection and selection of algae. Alternatively, attempts have been made to alter an alga into a more useful one by crossbreeding. However, crossbreeding and selection require a long period for cultivation and a lot of labor, and have not produced sufficient results.

Modification of land plants using genetic engineering techniques has been frequently carried out and produced some successful results. On the other hand, no successful case of modification using genetic engineering techniques or even expression of a transferred gene is known for marine macroalgae.

A promoter suitable for the host to be used is indispensable to in vivo expression of a gene. Accordingly, if one intends to express a gene in an alga, a promoter that operates in the alga is indispensable. However, there has been no known promoter derived from an alga to date. Therefore, it has been impossible to express a gene in an alga.

OBJECTS OF INVENTION

The present invention has been made in view of the prior art as described above. The main object of the present invention is to provide a promoter, an intron and a terminator that can be used to efficiently express a foreign useful gene in an alga and that are useful for breeding of an alga using genetic engineering techniques.

SUMMARY OF INVENTION

As a result of intensive studies, the present inventors have found that two elongation factor (EF) genes are expressed at high levels in all stages of the life cycle as a result of analyses of genes from *Porphyra yezoensis* Ueda which is generally eaten as food. Then, the present inventors have isolated the 5' upstream regions of the genes, and found that they have promoter activities. Furthermore, the present inventors have revealed the previously unknown genomic sequence of one of the EF genes. The present inventors have found an intron sequence and a terminator sequence in the genomic sequence, and shown that these sequences have activities of increasing expression efficiency of a transferred gene. Thus, the present invention has been completed.

The present invention is outlined as follows. The first aspect of the present invention relates to an isolated DNA that exhibits a promoter activity in an alga, which is selected from the group consisting of (a) to (c) below:

(a) a DNA having a nucleotide sequence of SEQ ID NO:9 or a portion thereof;

(b) a DNA that is capable of hybridizing with the DNA of (a) or a strand complementary thereto under stringent conditions; and (c) a DNA having a nucleotide sequence in which one or more nucleotide is substituted, deleted, inserted or added in the DNA of (a).

The second aspect of the present invention relates to an isolated DNA that exhibits an activity of increasing transcription efficiency of a gene in an alga, which is selected from the group consisting of (d) to (f) below:

(d) a DNA having a nucleotide sequence of SEQ ID NO:10 or a portion thereof;

(e) a DNA that is capable of hybridizing with the DNA of (d) or a strand complementary thereto under stringent conditions; and (f) a DNA having a nucleotide sequence in which one or more nucleotide is substituted, deleted, inserted or added in the DNA of (d).

The third aspect of the present invention relates to an isolated DNA that exhibits a promoter activity in an alga having the isolated DNA of the first aspect and the DNA of the second aspect which is located downstream of the isolated DNA of the first aspect being adjacent thereto or separated by a DNA fragment of 1 to 10,000 nucleotides therefrom. According to the third aspect, the isolated DNA is exemplified by one which has a nucleotide sequence from position 87 to position 1367 in SEQ ID NO:3.

The fourth aspect of the present invention relates to an isolated DNA that exhibits a terminator activity in an alga, which is selected from the group consisting of (g) to (i) below:

(g) a DNA having a nucleotide sequence of SEQ ID NO:11 or a portion thereof;

(h) a DNA that is capable of hybridizing with the DNA of (g) or a strand complementary thereto under stringent conditions; and (i) a DNA having a nucleotide sequence in which one or more nucleotide is substituted, deleted, inserted or added in the DNA of (g).

The fifth aspect of the present invention relates to a recombinant DNA in which an objective gene is linked, such that the gene can be expressed, to any one of the DNAs of the first to fourth aspects. According to the fifth aspect, the objective gene is exemplified by a protein-encoding nucleic acid, an antisense nucleic acid-encoding nucleic acid, a decoy-encoding nucleic acid or a ribozyme-encoding nucleic acid.

The sixth aspect of the present invention relates to a vector containing any one of the DNAs of the first to fifth aspects. According to the sixth aspect, the vector may be a plasmid vector or a virus vector.

The seventh aspect of the present invention relates to an alga into which the DNA of the fifth aspect is transferred, or that is transformed with the vector of the sixth aspect.

The eighth aspect of the present invention relates to an isolated DNA that encodes a polypeptide having an elongation factor activity, which is selected from the group consisting of (j) to (l) below:

(j) a DNA having a nucleotide sequence of SEQ ID NO:1 or a portion thereof;

(k) a DNA that is capable of hybridizing with the DNA of (j) or a strand complementary thereto under stringent conditions; and (l) a DNA having a nucleotide sequence in which one or more nucleotide is substituted, deleted, inserted or added in the DNA of (j).

The ninth aspect of the present invention relates to an isolated DNA that encodes a polypeptide having an elongation factor activity, which is selected from the group consisting of (m) to (o) below:

(m) a DNA having a nucleotide sequence of SEQ ID NO:2 or a portion thereof;

(n) a DNA that is capable of hybridizing with the DNA of (m) or a strand complementary thereto under stringent conditions; and (o) a DNA having a nucleotide sequence in which one or more nucleotide is substituted, deleted, inserted or added in the DNA of (m).

Using the DNA that exhibits a promoter activity, the DNA that exhibits an activity of increasing transcription efficiency and/or the DNA that exhibits a terminator activity of the present invention, a vector for genetically engineering algae is provided. The genetic engineering of algae opens a way to breeding of algae and, consequently, novel industrially useful algae can be provided.

Furthermore, the present invention enables production of a polypeptide having an elongation factor activity derived from an alga using genetic engineering techniques.

DETAILED DESCRIPTION OF THE INVENTION

Figure 1:
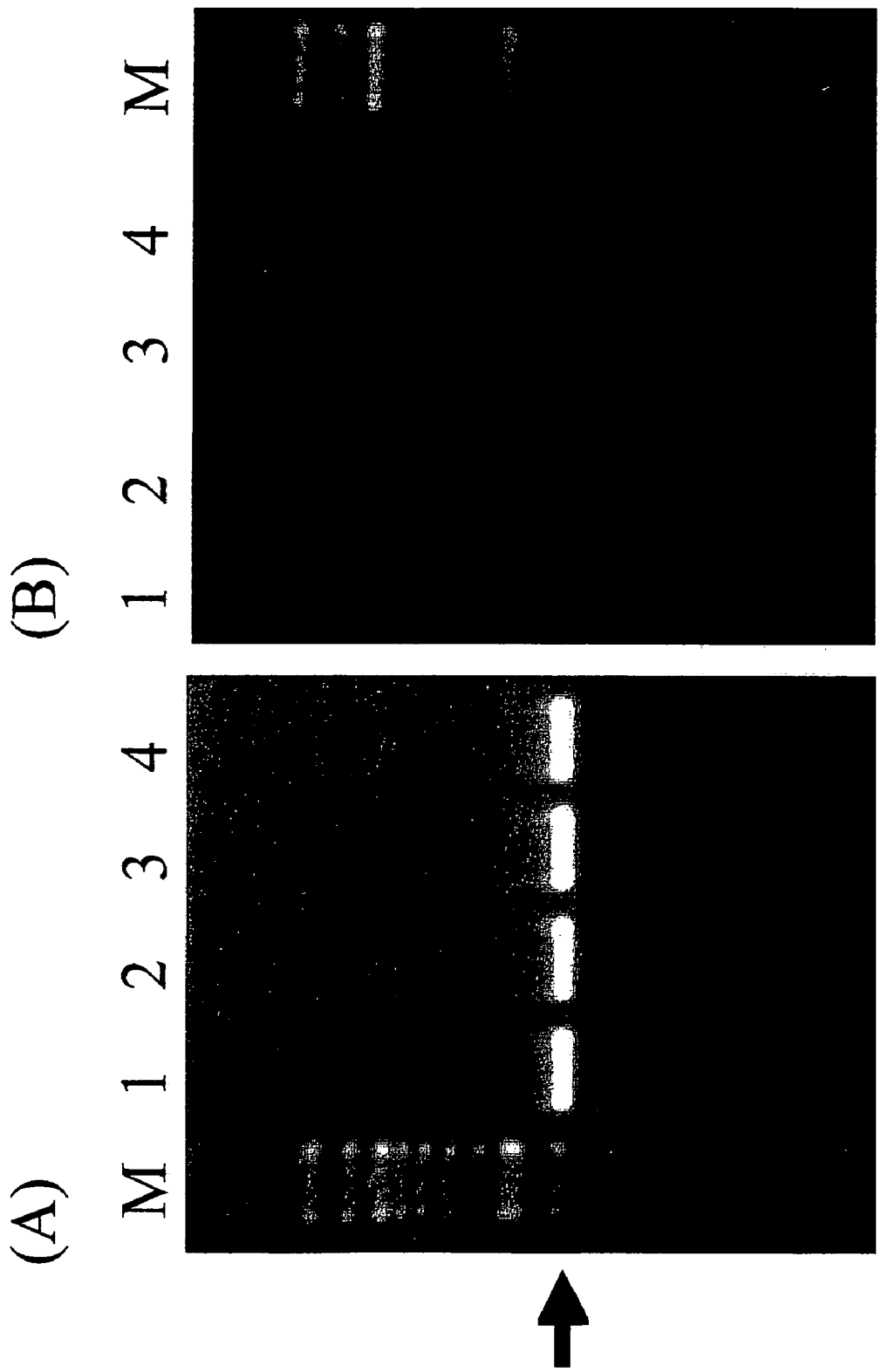
FIG. 1 illustrates the results of agarose gel electrophoresis for the A1 gene.

Hereinafter, the present invention will be described in detail.

As used herein, "a promoter" means a DNA that has a function of transcribing a gene, that is, a function of initiating synthesis of an mRNA using a DNA as a template. The promoter according to the present invention is not limited only to the above-mentioned function. It may include a TATA box or a TATA box-like region which is located 20 to 30 base pairs upstream of the transcription initiation site (+1) and is responsible for the function of initiating transcription from an accurate site by an RNA polymerase, or other regions necessary for expression control.

As used herein, "a promoter activity" refers to an ability and a function of producing the product of an objective gene inside or outside a host (an alga) upon transfer, into the host, of the objective gene linked downstream of a promoter such that the gene can be expressed.

The presence or strength of a promoter is generally expressed by means of a promoter activity which is determined by linking, downstream of the promoter, a gene encoding a protein that can be readily quantified (a reporter gene) such that the gene can be expressed, transferring the construct into a host and determining the amount of the expressed protein. It can be said that a promoter has an activity in the host into which it is transferred if one observes expression of an objective gene that is linked downstream of the promoter such that the gene can be expressed.

As used herein, "an intron" refers to a sequence that is present inside a gene or a transcript thereof and that is not included in the final RNA product of the gene.

The nucleotide sequence of an intron does not have information about an amino acid sequence. If a foreign gene containing an intron sequence is transferred into a host, the transcription efficiency may be increased and the objective protein encoded by the transferred gene may be produced at a high level in some cases. For example, a case of a higher plant is known (Tanaka, A. et al., Nucleic Acids Res., 18(23):6767-6770 (1990)).

A transcriptional efficiency can be determined, for example, by measuring the amount of a transcribed RNA according to a known method such as the Northern hybridization method or the RT-PCR method.

As used herein, "a terminator" refers to one having an activity of terminating transcription of an RNA. For example, the existence of a terminator can be examined by determining the size of a transcribed RNA according to a known method such as the Northern hybridization method.

There is no specific limitation concerning "an alga" according to the present invention. Examples thereof include algae belonging to any eukaryotes such as red algae (e.g., *Porphyra yezoensis* Ueda), brown algae (e.g., sea tangle (alga of the family Laminariaceae), *Undaria pinnatifida* or *Hizikia fusiforme*) and green algae (e.g., green layer (alga of the genus *Enteromorpha*)).

There is no specific limitation concerning "an objective gene" according to the present invention. Examples thereof include a protein-encoding nucleic acid, an antisense RNA-encoding nucleic acid, a decoy-encoding nucleic acid and a ribozyme-encoding nucleic acid which can be expressed in an alga.

"An exogenous gene" that is not functionally linked by nature to the DNA that exhibits a promoter activity, the DNA that exhibits an activity of increasing transcription efficiency or the DNA that exhibits a terminator activity according to the present invention may be used according to the present invention.

Examples of protein-encoding nucleic acids that can be expressed in algae include those derived from algae although it is not intended to limit the present invention. The objective gene according to the present invention include nucleic acids derived from microorganisms (e.g., bacteria, yeasts, actinomycetes, filamentous fungi, ascomycetes and basidiomycetes), plants and animals as well as viruses as long as they can be expressed in algae. The protein-encoding nucleic acids include nucleic acids that encode enzymes, receptors, cytokines, growth factors, factors involved in gene expression or control thereof and structural proteins although it is not intended to limit the present invention.

The DNA that exhibits a promoter activity according to the present invention (hereinafter referred to as the promoter) has a promoter activity in an alga. It is exemplified by the promoter of the EF1-alpha A2 gene from *Porphyra yezoensis* Ueda such as a DNA having a nucleotide sequence from position 87 to position 859 in SEQ ID NO:3 (i.e., the nucleotide sequence of SEQ ID NO:9) or a DNA containing a portion thereof. The promoter of the present invention may be any DNA within the nucleotide sequence of SEQ ID NO:9 as long as it has a promoter activity in an alga.

The promoters of the present invention also include a DNA that is capable of hybridizing to such a DNA or a strand complementary thereto under stringent conditions and that exhibits a promoter activity in an alga. Hybridization can be carried out according to a known method such as the method as described in T. Maniatis et al. (eds.), Molecular cloning: A Laboratory Manual, 2nd ed., 1989, Cold Spring Harbor Laboratory. The stringent conditions are exemplified by incubation with a probe at 65° C. overnight in a solution containing 6×SSC (1×SSC: 150 mM sodium chloride, 15 mM trisodium citrate dihydrate, pH 7.0) 0.5% SDS, 5× Denhardt's and 100 mg/ml of herring sperm DNA.

Furthermore, the promoters of the present invention include a DNA that has a nucleotide sequence in which one or more nucleotide is substituted, deleted, inserted or added in such a DNA and that exhibits a promoter activity in an alga.

It is possible to express an objective gene in an alga by transferring, into the alga, a recombinant DNA in which the objective gene is linked downstream of the promoter of the present invention such that the gene can be expressed. This enables breeding of an alga using genetic engineering techniques, production of a useful substance using an alga as a host, and the like.

The DNA that exhibits an activity of increasing transcription efficiency in an alga according to the present invention is exemplified by an intron of the EF1-alpha A2 gene from *Porphyra yezoensis* Ueda such as a DNA having a nucleotide sequence from position 878 to position 1331 in SEQ ID NO:3 (i.e., the nucleotide sequence of SEQ ID NO:10) or a DNA containing a portion thereof. The DNA of the present invention may be any DNA within the nucleotide sequence of SEQ ID NO:10 as long as it exhibits a activity of increasing transcription efficiency in an alga.

The DNAs of the present invention also include a DNA that is capable of hybridizing to such a DNA fragment or a strand complementary thereto under stringent conditions and that exhibits an activity of increasing transcription efficiency in an alga. Hybridization conditions are exemplified by those as described above.

Furthermore, the DNAs that exhibit an activity of increasing transcription efficiency of the present invention include a DNA that has a nucleotide sequence in which one or more nucleotide is substituted, deleted, inserted or added in such a DNA and that exhibits an activity of increasing transcription efficiency in an alga.

It is possible to increase transcription efficiency by further inserting the DNA that exhibits an activity of increasing transcription efficiency in an alga of the present invention at an appropriate site in a recombinant DNA in which the objective gene is linked to the above-mentioned DNA that exhibits a promoter activity of the present invention such that the gene can be expressed. For example, the appropriate site is located downstream of the promoter activity-exhibiting DNA being adjacent thereto or separated by a DNA fragment of 1 to 10,000 nucleotides therefrom.

The DNA that exhibits a terminator activity according to the present invention (hereinafter referred to as the terminator) is one exhibiting a terminator activity in an alga. It is exemplified by the terminator of the EF1-alpha A2 gene from *Porphyra yezoensis* Ueda such as a DNA having a nucleotide sequence from position 2718 to position 3764 in SEQ ID NO:3 (i.e., the nucleotide sequence of SEQ ID NO:11) or a DNA containing a portion thereof. The DNA of the present invention may be any DNA within the nucleotide sequence of SEQ ID NO:11.

The terminators of the present invention also include a DNA that is capable of hybridizing to such a DNA fragment or a strand complementary thereto under stringent conditions and that exhibits a terminator activity in an alga. Hybridization conditions are exemplified by those as described above.

Furthermore, the terminators of the present invention include a DNA that has a nucleotide sequence in which one or more nucleotide is substituted, deleted, inserted or added in such a DNA and that exhibits a terminator activity in an alga.

It is possible to increase the expression efficiency of an objective gene by further linking the fragment that exhibits a terminator activity of the present invention downstream of a recombinant DNA in which the objective gene is linked to the above-mentioned DNA that exhibits a promoter activity of the present invention such that the gene can be expressed optionally, the expression efficiency of the objective gene can be further increased by further incorporating the DNA that exhibits an activity of increasing transcription efficiency of a gene in an alga of the present invention.

The DNA that encodes a polypeptide having an elongation factor activity according to the present invention (hereinafter referred to as the EF gene) is exemplified by a DNA having a nucleotide sequence of SEQ ID NO:1 or a portion thereof, a DNA having a nucleotide sequence of SEQ ID NO:2 or a portion thereof, a DNA having a nucleotide sequence of SEQ ID NO:3 or a portion thereof, or a DNA that encodes a polypeptide having an amino acid sequence of SEQ ID NO:8 or a portion thereof. Preferable examples of the EF genes according to the present invention include a DNA having a nucleotide sequence from position 79 to position 1425 in SEQ ID NO:1, and a DNA having a nucleotide sequence from position 65 to position 1401 in SEQ ID NO:2, as well as a DNA having a nucleotide sequence from position 1368 to position 2714 in SEQ ID NO:3. In addition, it may be a DNA that encodes any polypeptide within the amino acid sequence of SEQ ID NO:8.

The DNAs of the present invention also include a DNA that is capable of hybridizing to such a DNA fragment or a strand complementary thereto under stringent conditions and that encodes a polypeptide having an EF activity. Hybridization conditions are exemplified by those as described above.

Furthermore, the DNAs that encode a polypeptide having an EF activity of the present invention include a DNA that has a nucleotide sequence in which one or more nucleotide is substituted, deleted, inserted or added in such a DNA and that encodes a polypeptide having an EF activity.

The DNA that is capable of hybridizing to the above-mentioned DNA or a strand complementary thereto under stringent conditions, or the DNA that has a nucleotide sequence in which one or more nucleotide is substituted, deleted, inserted or added in the above-mentioned DNA is exemplified by a DNA having a homology of for example 90% or more, preferably 95% or more, more preferably more than 97% with the above-mentioned DNA.

For example, an EF activity can be measured according to the method as described in Shalak, V. F. et al., Ukr. Biokhim. Zh., 69:104-109 (1997).

A recombinant DNA in which an objective gene is linked to the promoter, the DNA that exhibits an activity of increasing transcription efficiency in an alga, or the DNA that exhibits a terminator activity of the present invention or a combination thereof such that the gene can be expressed can be transferred into an alga with or without mediation of a vector. A plasmid vector or a virus vector can be preferably used as a vector.

There is no specific limitation concerning the morphology of the alga into which a DNA is to be transferred. It is possible to use an alga with any morphology such as a filamentous thallus, a spore, a foliose thallus, a cultured cell or a protoplast.

There is no specific limitation concerning the method for transferring a DNA into an alga. A known method such as the particle gun-mediated transfer method may be used.

For example, the promoter of the present invention can be isolated from *Porphyra yezoensis* Ueda as follows.

*Porphyra yezoensis* Ueda is an alga that belongs to the division Rhodophyta, the class Rhodophyceae, the subclass Protoflorideophycidae, the order Bangiales, the family Bangiaceae. It is naturally growing around the western and southern parts of Hokkaido and the northern part of Honshu in Japan as well as around Korean Peninsula.

*Porphyra yezoensis* Ueda is an alga that is generally eaten as food, flourishingly farmed and widely put on the market. A naturally growing alga harvested from the sea, a farmed alga or a commercially available alga can be used for the present invention. A line established according to a known method (Kuwano, K. et al., Plant Sci., 116(1):117-124 (1996)) can also be used for the present invention.

<Selecting a Candidate Gene for Isolating a Promoter>

In order to find a promoter for expressing a foreign gene at a high level, it is necessary to find a gene expressed in an alga as a host at a high level, isolate its genomic sequence and analyze its structure.

Sequences of expressed sequence tags (ESTs) from *Porphyra yezoensis* Ueda are available to the public from the home page of Kazusa DNA Research Institute kazusa.or.jp/en/plant/porphyra/EST/.

EST clustering analyses are carried out for the sequence information, for example, using the PARACEL CLUSTERING PACKAGE software (Paracel). It is considered that a gene for which a large number of EST sequences are determined to belong to the identical cluster as a result of the clustering analyses may possibly be expressed at a high level. Thus, the promoter of such a gene can serve as a candidate sequence to be isolated.

For example, two such genes, the *Porphyra yezoensis* elongation factor EF1-alpha A1 gene and the *Porphyra yezoensis* elongation factor EF1-alpha A2 gene (hereinafter referred to as the A1 gene and the A2 gene, respectively) can be selected and used as materials for isolating the promoters of the present invention.

The cDNA for the candidate gene can be cloned using, as a probe, an EST sequence contained in the cluster for the candidate gene selected as a result of the clustering analyses, a consensus sequence obtained by assembling, or a portion thereof. For example, a primer can be designed based on the consensus sequence obtained by assembling the EST sequences belonging to the A1 gene, a fragment of the A1 gene can be amplified by PCR using the primer, and the fragment can be used as a probe.

The cDNA for the A1 gene represented by SEQ ID NO:1. is an example of cDNAs for novel candidate genes isolated according to the present invention as described above.

<Examining whether or not a Gene is Expressed at High Levels Throughout the Algal Life Cycle>

It is possible to examine whether or not a candidate gene is expressed at high levels throughout the algal life cycle by measuring the amounts of expressed mRNAs at various stages of the algal life cycle by means of Northern hybridization using the DNA sequence of the candidate gene as a probe.

A known method (e.g., the guanidine thiocyanate method or the phenol/chloroform method) may be used for extracting a total RNA from an algal tissue. The extracted total RNA can be used for measuring the amount of expressed mRNA of interest.

For example, total RNAs can be extracted from the alga *Porphyra yezoensis* Ueda at the following stages of the life cycle using the modified phenol/chloroform method and subjected to agarose gel electrophoresis followed by Northern hybridization using the candidate gene DNA as a probe:

(1) the stage of gametophyte with unformed monospore;
(2) the stage of gametophyte with formed monospore;
(3) the stage of vegetatively growing gametophyte after monospore formation; and
(4) the stage of filamentous sporophyte.

Alternatively, it is possible to analyze the expression pattern using RT-PCR. In this case, an analysis in which family genes are distinguished more strictly is made possible by designing a specific primer.

For example, the expression levels of the candidate gene at the above-mentioned stages can be determined by carrying out RT-PCRs using primers for the translated region and the untranslated region of the cDNA for the gene, total RNAs extracted at the respective stages using the guanidine thiocyanate method as templates and TaKaRa RNA PCR Kit Ver. 2.1 (Takara Shuzo) or the like.

Thus, a gene that is expressed at high levels at the respective stages in an alga can be found.

<Cloning a Promoter-containing Region>

A promoter-containing region of the gene expressed at high levels at the respective stages selected as described above can be isolated, for example, by screening a genomic library for a genomic DNA of the gene.

The plaque hybridization method using a genomic library, the PCR method in which an unknown sequence is amplified using a genomic DNA based on a known sequence and the like can be used for cloning a promoter for a gene expressed at a high level in an alga although it is not intended to limit the present invention.

The genomic DNA fragment containing the novel elongation factor EF1-alpha A2 gene represented by SEQ ID NO:3 isolated according to the present invention is an example of genes expressed at high levels at the respective stages. It was shown that the sequence contains a promoter sequence, an intron sequence and a terminator sequence by comparison of the A2 gene (SEQ ID NO:3) with the cDNA sequences (SEQ ID NO:1) and the EST sequences obtained as a result of the clustering analyses, as well as transcription factor searches, coding region searches and intron-exon searches.

Specifically, the nucleotide sequence of SEQ ID NO:3 covers the entire genomic sequence of the elongation factor EF1-alpha A2 gene. In the sequence, the nucleotide sequence from position 1368 to position 2717 is the A2 polypeptide-encoding sequence (including the termination codon), the nucleotide sequence from position 878 to 1331 is the sequence of the first intron, the nucleotide sequence from position 1 to 859 is the promoter sequence, and the nucleotide sequence from position 2718 to 3764 is the terminator sequence.

Comparison of the nucleotide sequence of SEQ ID NO:3 with the cDNA sequence (SEQ ID NO:1) and the EST sequences obtained as a result of the clustering analyses revealed the sequence of cDNA for the A2 gene. This sequence is shown in SEQ ID NO:2. In this sequence, the region contained in the nucleotide sequence of SEQ ID NO:3 is the exon region of the EF1-alpha A2 gene.

The promoter isolated according to the present invention is a DNA that exhibits a promoter activity in an alga, and can be used to express an objective gene in an alga. Also, a DNA that exhibits a promoter activity and is capable of hybridizing with the sequence under stringent conditions, or a DNA that has substitution, deletion, insertion or addition of nucleotide(s) in the sequence such that the promoter activity is not abolished can be used for the above-mentioned purpose.

The terminator isolated according to the present invention is a DNA that exhibits a terminator activity in an alga, and can be used to increase expression efficiency of an objective gene in an alga. Also, a DNA that exhibits a terminator activity and is capable of hybridizing with the sequence under stringent conditions, or a DNA that has substitution, deletion, insertion or addition of nucleotide(s) in the sequence such that the terminator activity is not abolished can be used for the above-mentioned purpose.

In higher plants, it is known that transcription efficiency is increased by using a gene containing an intron sequence for transfer, and the objective protein is produced from the transferred gene at a high level in some cases. The first intron isolated according to the present invention can be used for increasing transcription efficiency of an objective gene to be expressed in an alga. A DNA that is capable of hybridizing with the sequence under stringent conditions, or a DNA that has substitution, deletion, insertion or addition of nucleotide(s) in the sequence can be used for the above-mentioned purpose as long as it exhibits an activity of increasing transcription efficiency.

The exon region isolated according to the present invention is a sequence that encodes a novel elongation factor (EF) from an alga, the EF1-alpha A2 polypeptide. This sequence can be used for production of the EF1-alpha A2 polypeptide using genetic engineering techniques. In addition, the sequence can be used for a probe or a primer for screening a further novel EF gene, in particular a novel EF gene from an alga.

The DNA of the present invention disclosed herein can be isolated as described above. Alternatively, it can be chemically synthesized based on the sequence information disclosed herein.

A DNA that exhibits a promoter activity in an alga has been isolated for the first time according to the present invention. Then, the isolation enabled artificial expression of an objective gene in an alga which had been impossible to date. Furthermore, a DNA that exhibits a terminator activity and an intron have been isolated from an alga for the first time. Then, it is now possible to increase expression efficiency of an objective gene in an alga. The above enables production of a useful substance in an alga using genetic engineering techniques. In addition, it enables breeding of an alga, which traditionally had to rely on very inefficient crossbreeding, with efficiency using genetic engineering techniques.

A novel elongation factor gene has been isolated from an alga for the first time according to the present invention. Then, it is now possible to produce using genetic engineering techniques an elongation factor from an alga, which could be obtained only from a harvested or cultured alga.

EXAMPLES

The following examples further illustrate the present invention in detail but are not to be construed to limit the scope thereof.

Example 1

Preparation of mRNAs from *Porphyra yezoensis* Ueda at Respective Stages

1. Materials

Leafy gametophytes and filamentous sporophytes from *Porphyra yezoensis* Ueda TU-1, a pure line of *Porphyra yezoensis* Ueda established by Kuwano, K. et al., Plant Sci., 116(1):117-124 (1996), were used.

2. Culture Conditions

The leafy gametophytes were cultured with circulation at 15° C. with 10 hours in the light (light volume of 80 µE/(m²·s); cool white fluorescent lamp) and 14 hours in the dark in a 1-1 side-arm flat bottom glass flask (PYREX) containing the ESL medium (3.5% (w/v) SEALIFE power (Marine Tech), 1% (v/v) $ESS_2$) with aeration (air sterilized by filtration, 0.12 l/min).

The filamentous sporophytes were statically cultured at 25° C. with 24 hours in the light (light volume of 17 µE/(m²·s); cool white fluorescent lamp) in a 500-ml glass Erlenmeyer flask containing the ESL medium.

3. Extraction of Total RNA

Total RNAs were extracted from *Porphyra yezoensis* Ueda TU-1 at the following stages: 1- to 2-mm-long leafy gametophyte prior to monospore formation, 2-mm-long leafy gametophyte which had been subjected to induction of monospore release for 30 minutes, 1- to 2-cm-long leafy gametophyte, and filamentous sporophyte.

Total RNAs were extracted according to the phenol/chloroform method as described in Apt, K. E. et al., Mol. Gen. Genet., 246(4):455-464 (1995) with partial modification.

The procedure used for extracting a total RNA from an alga is described below.

After removing water using a paper towel, a cultured alga was weighed. 1.2 g of the alga was ground using a mortar and a pestle in liquid nitrogen. The ground alga was transferred, using a spoon which had been precooled in liquid nitrogen, into a 50-ml centrifuge tube containing 16.8 ml of an extraction buffer (100 mM Tris-HCl (pH 8.0), 1.5 M NaCl, 20 mM EDTA, 20 mM DTT (dithiothreitol) and 2% CTAB (cetyltrimethylammonium bromide)). The mixture was mixed using a shaker NR-1 (TAITEC) at 110 rpm/min at room temperature for 15 minutes. Then, an equal volume of chloroform was added thereto, and the mixture was stirred.

The mixture was centrifuged to collect an upper layer. ⅓ volume of ethanol was slowly added dropwise thereto and mixed. The mixture was centrifuged to remove a precipitate mainly composed of polysaccharides. An equal volume of chloroform was added to the supernatant and stirred. The mixture was centrifuged to collect a supernatant. This procedure was repeated until the supernatant was decolored.

The supernatant was collected. ½ volume of 9 M LiCl and 1/100 volume of β-mercaptoethanol were added to the supernatant. The mixture was allowed to stand at −20° C. overnight. The resulting precipitate was collected by centrifugation, dissolved in 50 µl of DEPC (diethyl pyrocarbonate)-treated water and extracted with an equal volume of phenol/chloroform (1:1). This extraction procedure was repeated until the intermediate layer disappeared.

The upper layer was collected. 1/10 volume of 3 M sodium acetate and 2 volumes of ethanol were added to the upper layer and mixed. The resulting precipitate was collected by centrifugation, rinsed with 75% ethanol and air-dried.

The precipitate was dissolved in 90 l of DEPC-treated water. 1 ml of ISOGEN (Wako Pure Chemical Industries) was added thereto. The mixture was allowed to stand at room temperature for 5 minutes. 0.2 ml of chloroform was added thereto. After stirring, the mixture was allowed to stand at room temperature for 2 to 3 minutes.

The mixture was centrifuged to obtain a supernatant. 0.5 ml of isopropanol was added thereto. The resulting precipitate was collected by centrifugation, rinsed with 75% ethanol, air-dried and dissolved in 400 µl of DEPC-treated water.

Furthermore, for removing the remaining polysaccharides, 200 µl of a high salt precipitation solution (1.2 M NaCl, 0.8 M trisodium citrate dihydrate, pH not adjusted) and 200 µl of isopropanol were added thereto, and the mixture was centrifuged. The resulting precipitate was rinsed with 75% ethanol, air-dried and dissolved in 100 µl of DEPC-treated water.

The concentration and the purity of the total RNA extracted as described above were determined using a spectrophotometer UV-2002 (Shimadzu). In addition, the total RNA was subjected to electrophoresis on 1.0% agarose gel to confirm that it was not degraded.

An mRNA was separated from the total RNA extracted as described above using Oligotex™-dT30 super (Roche) according to the attached instructions.

Example 2

Clustering Analyses of *Porphyra yezoensis* Ueda EST Sequences

*Porphyra yezoensis* Ueda EST sequences used for analyses were down-loaded from the home page of Kazusa DNA Research Institute kazusa.or.jp/en/plant/porphyra/EST/. A total of 10154 *Porphyra yezoensis* Ueda EST sequences down-loaded were subjected to clustering of sequences using PARACEL CLUSTERING PACKAGE (Paracel).

As a result, 8243 sequences were classified into 1140 clusters while 1911 sequences belonged to no cluster.

A list of cluster IDs for 50 clusters to which the largest numbers of sequences belong is shown in Tables 1 to 4 below. It is considered that if a gene is expressed at a higher level, the number of sequences belonging to the cluster (sequence count) is larger.

Furthermore, consensus sequences of contigs generated by assembling the sequences belonging to the respective clusters were subjected to homology searches of the nucleotide database (a database of non-redundant nucleic acids) of NCBI (National Center for Biotechnology Information) ncbi.nih.go/ using the BLAST program (Altschul, S. F. et al., Nucleic Acids Res., 25(17):3389-3402 (1997)).

Among the results of the homology searches, the contig IDs, the numbers of sequences (sequence counts) and the GenBank accession nos. for the contigs of the clusters for which the highest hit scores were observed are shown in Tables 1 to 4 along with the numbers (No.). The scores and the E values are also shown in Tables 1 to 4.

TABLE 1

Clustering of *Porphyra yezoensis* Ueda EST sequences

| No. | Cluster ID | Sequence Count | Contig ID | GenBank Accession No | Score | E value |
|---|---|---|---|---|---|---|
| 1 | 145 | 687 | 3 | X60733.1 | 220 | 8.00E−55 |
| 2 | 13 | 500 | 5 | L26199.1 | 3495 | 0 |
| 3 | 0 | 394 | 3 | X57263.1 | 163 | 8.00E−38 |
| 4 | 40 | 131 | 1 | U65510.1 | 42 | 0.041 |
| 5 | 17 | 113 | B1 | D10167.1 | 42 | 0.21 |
| 6 | 72 | 90 | 1 | AC003030.1 | 42 | 0.47 |
| 7 | 16 | 80 | 1 | NM_003654.1 | 48 | 0.006 |
| 8 | 107 | 76 | 1 | M72894.1 | 48 | 0.005 |
| 9 | 261 | 75 | 1 | AC006214.1 | 44 | 0.075 |
| 10 | 25 | 60 | 1 | Y00545.1 | 42 | 0.11 |
| 11 | 284 | 58 | 2 | Z79601.1 | 40 | 0.94 |
| 12 | 459 | 57 | 1 | U77477.1 | 46 | 0.019 |
| 13 | 38 | 49 | 1 | AL009198.1 | 42 | 0.28 |
| 14 | 4 | 47 | 1 | AJ012146.1 | 38 | 4.3 |

TABLE 2

Clustering of *Porphyra yezoensis* Ueda EST sequences (continued 1)

| No. | Cluster ID | Sequence Count | Contig ID | GenBank Accession No | Score | E value |
|---|---|---|---|---|---|---|
| 15 | 189 | 47 | 1 | X62072.1 | 46 | 0.027 |
| 16 | 74 | 46 | 1 | AC004476.1 | 48 | 0.002 |
| 17 | 334 | 41 | 1 | AB025619.1 | 44 | 0.052 |
| 18 | 120 | 40 | 1 | AL008728.1 | 44 | 0.037 |
| 19 | 291 | 38 | 1 | AF080121.1 | 488 | E−135 |
| 20 | 350 | 38 | 2 | D86993.1 | 40 | 0.94 |
| 21 | 508 | 38 | 1 | AC006213.1 | 42 | 0.18 |
| 22 | 5 | 37 | 1 | M11779.1 | 42 | 0.28 |
| 23 | 114 | 37 | 1 | AF034863.1 | 40 | 0.96 |
| 24 | 401 | 35 | 1 | AB025615.1 | 42 | 0.33 |
| 25 | 97 | 32 | 1 | M88684.1 | 551 | E−155 |
| 26 | 515 | 32 | 1 | AL021707.2 | 42 | 0.32 |
| 27 | 56 | 31 | 1 | X97257.1 | 44 | 0.047 |
| 28 | 676 | 31 | 1 | Z98747.1 | 42 | 0.2 |
| 29 | 320 | 30 | 1 | Z79702.1 | 40 | 0.98 |
| 30 | 369 | 30 | 1 | D86051.1 | 58 | 2.00E−06 |

TABLE 3

Clustering of *Porphyra yezoensis* Ueda EST sequences (continued 2)

| No. | Cluster ID | Sequence Count | Contig ID | GenBank Accession No | Score | E value |
|---|---|---|---|---|---|---|
| 31 | 700 | 30 | 1 | AB005232.1 | 44 | 0.043 |
| 32 | 9 | 29 | 1 | U08844.1 | 1889 | 0 |
| 33 | 348 | 29 | 1 | U58679.1 | 74 | 5.00E−11 |
| 34 | 812 | 29 | 1 | AF071752.1 | 50 | 8.00E−04 |
| 35 | 14 | 28 | 1 | AC005615.1 | 42 | 0.62 |
| 36 | 251 | 28 | 1 | AF064842.1 | 46 | 0.024 |
| 37 | 383 | 28 | 1 | AJ012478.1 | 220 | 4.00E−55 |
| 38 | 806 | 28 | 1 | AF117660.1 | 40 | 0.75 |
| 39 | 122 | 27 | 1 | NM_003330.1 | 40 | 1 |
| 40 | 321 | 26 | 1 | X61361.1 | 42 | 0.19 |
| 41 | 564 | 26 | 1 | AB022100.1 | 40 | 0.83 |
| 42 | 132 | 25 | 1 | AF055296.1 | 64 | 9.00E−08 |
| 43 | 279 | 25 | 1 | U13168.1 | 86 | 2.00E−14 |
| 44 | 382 | 25 | 1 | M74056.1 | 42 | 0.32 |
| 45 | 140 | 24 | 1 | D38516.1 | 188 | 2.00E−45 |
| 46 | 451 | 24 | 1 | X80345.1 | 593 | E−167 |

TABLE 4

Clustering of *Porphyra yezoensis* Ueda EST sequences (continued 3)

| No. | Cluster ID | Sequence Count | Contig ID | GenBank Accession No | Score | E value |
|---|---|---|---|---|---|---|
| 47 | 672 | 24 | 1 | Z97055.1 | 44 | 0.056 |
| 48 | 662 | 23 | 1 | AP000133.1 | 40 | 0.67 |
| 49 | 34 | 22 | 1 | D12631.1 | 74 | 6.00E−11 |
| 50 | 399 | 22 | 1 | AC005288.1 | 42 | 0.29 |

The titles for the GenBank accession nos. of the hits are shown in Tables 5 to 8 in the columns under Hit name.

TABLE 5

Titles for accession nos. of hits.

| No.* | Hit Name |
|---|---|
| 1 | *O. cuniculus* mRNA for gamma-non muscle actin. |
| 2 | *Porphyra leucosticta* DNA fragment. |
| 3 | Chicken gene for histone H2B-IV. |
| 4 | *Rhodospirillum rubrum* CO-induced hydrogenease operon (cooM, cooK, cooL, cooX, cooU, cooH) genes, iron sulfur protein (cooF) gene, carbon, monoxide dehydrogenase (cooS) gene, carbon monooxide dehydrogenase accessory proteins (cooC, cooT, cooJ) genes, putative transcriptional activator (cooA) gene, nicotinate-nucleotide pyrophosphorylase (nadC) gene, complete cds, L-aspartate oxigenase (nadB) gene, and alkyl hydroperoxide reductase (ahpC) gene, partial cds. |

TABLE 5-continued

Titles for accession nos. of hits.

| No.* | Hit Name |
|---|---|
| 5 | Chicken rig gene for ribosomal protein S15. |
| 6 | *Homo sapiens* chromosome 19, overlapping cosmids R29828 and F25496, complete sequence. |
| 7 | *Homo sapiens* carbohydrate (chondroitin 6/keratan) sulfotransferase 1 (CHST1), mRNA. |
| 8 | Soybean ferritin (SOF-H2) mRNA, partial cds. |
| 9 | *Drosophila melanogaster*, chromosome 2L, region 36A7-36A13, P1 clones DS04680 and DS00592, complete sequence. |
| 10 | *Bordetella pertussis* cya gene for calmodulin-sensitive adenylate cyclase. |
| 11 | *Caenorhabditis elegans* cosmid K09A9, complete sequence. |
| 12 | *Oryctolagus cuniculus* coagulation factor VII mRNA, complete cds. |
| 13 | *Mycobacterium tuberculosis* H37Rv complete genome; segment 144/162. |
| 14 | *Ovis aries* cyp19 gene, exon 4. |

*No. in Table 5 corresponds to No. in Table 1.

TABLE 6

Titles for accession nos. of hits. (continued 1)

| No.* | Hit Name |
|---|---|
| 15 | *Erwinia chrysanthemi* kdgR gene for KdgR gene for KdgR repressor. |
| 16 | *Homo sapiens* chromosome 19, cosmid R29388, complete sequence. |
| 17 | *Arabidopsis thaliana* genomic DNA, chromosome 5, P1 clone: MBA10. |
| 18 | Human DNA sequence from clone 125N5 on chromosome 6q26-27. Contains a putative novel gene, ESTs, STSs and GSSs, complete sequence. |
| 19 | *Arabidopsis thaliana* BAC T25C13. |
| 20 | *Homo sapiens* immunoglobulin lambda gene locus DNA, clone: 23C6. |
| 21 | *Homo sapiens*, clone hRPK.15_A_1, complete sequence. |
| 22 | Pig calpain I light subunit mRNA, complete cds. |
| 23 | *Rattus norvegicus* synaptic scaffolding molecule (S-SCAM) mRNA, complete cds. |
| 24 | *Arabidopsis thaliana* genomic DNA, chromosome 3, TAC clone: K5K13. |
| 25 | *Aglaothamnion neglectum* ubiquitin mRNA, complete cds. |
| 26 | Human DNA sequence from clone RP3-508115 on chromosome 22q12-13. Contains the gene for GTPBP1 (GTP binding protein 1), two novel genes KIAA0063 and KIAA0668, a novel gene based on ESTs and cDNA, a pseudogene similar to AOP1 (antioxidant protein 1), ESTs, STSs, GSSs, a genomic marker D22S272, a CA repeat and CpG island, complete sequence. |
| 27 | Pseudorabies virus UL[5, 6, 7, 8, 8.5, 9, 10, 11, 12, 13] genes. |
| 28 | Human DNA sequence from clone 37J18 on chromosome 1p36.2-36.3. Contains a putative novel gene, ESTs and GSSs, complete sequence. |
| 29 | *Mycobacterium tuberculosis* H37Rv complete genome; segment 102/062. |
| 30 | *Porphyridium purpureum* mRNA for carbonic anhydrase, complete cds. |

*No. in Table 6 corresponds to No. in Table 2.

TABLE 7

Titles for accession nos. of hits. (continued 2)

| No.* | Hit Name |
|---|---|
| 31 | *Arabidopsis thaliana* genomic DNA, chromosome 5, P1 clone: MBG8. |
| 32 | *Porphyra purpurea* elongation factor EF1-alpha (tef-c) mRNA. |
| 33 | *Porphyridium cruentum* light-harvesting complex I polypeptide (Lhca1) mRNA, complete cds. |
| 34 | *Neurospora crassa* protein phosphatase-Z-link serine/threonine protein phosphatase (pzl-1) mRNA, complete cds. |
| 35 | *Homo sapines* chromosome 19, cosmid R28058, complete sequence. |
| 36 | *Homo sapiens* map 2q30-p32; 202.6 cR from top repeat reagion, complete sequence. |
| 37 | *Salmo salar* mRNA for Ran protein. |
| 38 | *Triticum aestivum* S-adenosylmethionine decarboxylase precursor, mRNA, complete cds. |
| 39 | *Homo sapiens* thioredoxin reductase 1 (TXNRD1), mRNA. |
| 40 | *E. gracilis* gene for light harvesting chlorophyll a/b binding protein of photosystem II. |
| 41 | *Mus musculus* mRNA for T-cadherin, complete cds. |
| 42 | *Zantedeschia aethiopica* geranylgeranyl reductase mRNA, partial cds. |
| 43 | *Chlamydomonas reinhardtii* YptC1 (yptC1) gene, complete cds. |
| 44 | *Myxococcus xanthus* protein U gene, complete cds. |
| 45 | Human Rab11B mRNA. |
| 46 | *H. catenoides* gene for 28S ribosomal RNA. |

*No. in Table 7 corresponds to No. in Table 3.

TABLE 8

Titles for accession nos. of hits. (continued 3)

| No.* | Hit Name |
|---|---|
| 47 | Human DNA sequence from clone RP3-388M5 on chromosome 22. Contains an RPL4 (60S Ribosomal Protein 4) pseudogene, the HMG17L1 gene for high-mobility group (non-histone chromosomal) protein 17-like 1, the gene for a novel Sulfotransferase (sulfokinase, EC 2.8.2.1) like protein, the gene for a GS2 like protein, ESTs, STSs, GSSs and four putative CpG island, complete sequence. |
| 48 | *Homo sapiens* genomic DNA of 21q22.1, GART and AML, f43D11-119B8 reagion, segment 8/10, complete sequence. |
| 49 | Rice mRNA for ribosomal protein L7A, complete cds. |
| 50 | *Homo sapiens* chromosome 17, clone hCIT.131_K_11, complete sequence. |

*No. in Table 8 corresponds to No. in Table 4.

The hit gene titles were screened for a hit of mRNA or cDNA (not a clone of a genomic sequence or a fragment thereof), or a hit containing the term *Porphyra*. As a result, genes from organisms closely related to *Porphyra yezoensis* Ueda were found.

Furthermore, two mRNA or cDNA sequences from organisms closely related to *Porphyra yezoensis* Ueda, the cluster ID no. 13 (No. 2 in Tables 1 and 5) and the cluster ID no. 9 (No. 32 in Tables 3 and 7), were found among the 50 clusters by screening for a gene sequence expressed at a high level.

The cluster ID no. 13, one of the two mRNA or cDNA sequences, is highly homologous to 18S rRNA. As a result of homology searches using the consensus sequence of the contig 1 of the cluster ID no. 9, a hit was found for *Porphyra purpurea* elongation factor EF1-alpha (tef-c) mRNA (Gen- Bank accession no. U08844). It was considered to be one of the most suitable candidates for the purpose of the present invention.

In addition, it was found that there were mismatches in the results of assembling of the contig 1 of the cluster ID no. 9, the sequences are divided into two groups and, in particular, the sequences of the untranslated regions at the 5' ends are clearly distinct.

Based on the above-mentioned results, the genes for the two groups were designated as Porphyra yezoensis elongation factor EF1-alpha A1 and elongation factor EF1-alpha A2 genes (hereinafter referred to as the A1 and A2 genes).

Example 3

Cloning, Sequencing and Sequence Analysis of Full Length cDNA for A1 Gene

1. Materials

A cultured single algal leafy gametophyte of Porphyra yezoensis Ueda TU-1 (established by Kuwano, K. et al., Plant Sci., 116(1):117-124 (1996)) was used as a material for cDNA cloning.

2. Culture Conditions

Porphyra yezoensis Ueda TU-1 was cultured with circulation at 15° C. under short-day conditions with 10 hours in the light (light volume of 80 $\mu E/(m^2 \cdot s)$; cool white fluorescent lamp) and 14 hours in the dark in a 1-1 side-arm flat bottom flask (PYREX) containing the ESL medium with aeration (air sterilized by filtration through 0.2-μm filter (ADVANTEC), 0.25 l/min). The medium was exchanged every seven days.

3. RNA Extraction

Total RNA was extracted from 1.2 g of the cultured single algal leafy gametophyte of Porphyra yezoensis Ueda TU-1 according to the method as described in Example 1.

4. Preparation of Probe for cDNA Library Screening

DNA was extracted from Porphyra yezoensis Ueda TU-1 according to the method as described in Kitade et al., J. Phycol., 32:496-498 (1996).

PCR was carried out using the DNA as a template, AmpliTaq Gold (Applied Biosystems), and two primers, PYEF1 (SEQ ID NO:7) and PYEFR1 (SEQ ID NO:5). These primers were designed based on the results of EST clustering as described in Example 2 for amplifying a highly conservative sequence containing a motif of an elongation factor EF1-alpha gene. The PCR was carried out as follows: preheating at 94° C. for 2 minutes; 30 cycles of 94° C. for 1 minute, 53° C. for 1 minute and 72° C. for 2 minutes; and final reaction at 72° C. for 10 minutes.

The resulting about 170-bp PCR product was subjected to electrophoresis on 1.5% agarose gel. The band of interest was recovered from the gel using Geneclean II kit (Bio101), and ligated to a vector for TA cloning, pT7Blue (Novagen), using DNA Ligation Kit Ver. 2 (Takara Shuzo). The ligation mixture was transferred into Escherichia coli JM109 competent cells (Takara Shuzo) according to a conventional method (Maniatis et al. (eds.), Molecular Cloning, a Laboratory Manual, Cold Spring Harbor, 1989). Colonies of Escherichia coli transformants were obtained by culturing on LB agar medium containing ampicillin.

Colonies of transformants were picked up at random. The lengths of inserts in the plasmids harbored in the colonies were determined by electrophoresis of products of PCR amplification using T7 promoter primer (Novagen) which has a sequence in the vector pT7Blue and a primer M4 (Takara Shuzo). An Escherichia coli colony having a DNA fragment of the expected length was selected.

The selected colony of Escherichia coli transformant was subjected to liquid culture. The plasmid was then extracted using QIAGEN Plasmid Mini Kit (Qiagen).

The nucleotide sequence was determined according to the cycle sequencing method using the plasmid as a template and dRhodamine Terminator Cycle Sequencing FS Ready Reaction Kit (Applied Biosystems). The cycle sequencing reaction was carried out as follows: preheating at 96° C. for 2 minutes; 25 cycles of 96° C. for 10 seconds, 50° C. for 5 seconds and 60° C. for 4 minutes.

The resulting reaction product was purified according to a simplified method utilizing ethanol precipitation. The nucleotide sequence was then determined using ABI PRISM 310 Genetic Analyzer (Applied Biosystems). Plasmid extraction and nucleotide sequence determination were carried out according to the attached instructions.

After the nucleotide sequence determination, homology searches of a nucleic acid sequence database were carried out using the BLAST program available to the public from NCBI (Altschul, S. F. et al., Nucleic Acids Res., 25(17):3389-3402 (1997)) in order to confirm if the determined sequence was the sequence of interest. The results of searches revealed that the determined sequence matched the best to the sequence of the A1 gene predicted based on the clustering and assembling.

PCR was carried out again using the plasmid whose sequences had been determined as a template as well as the primers PYEF1 (SEQ ID NO:7) and PYEFR1 (SEQ ID NO:5) under the above-mentioned conditions. The PCR product was labeled with digoxigenin using PCR DIG Labeling Mix (Roche). After the labeling reaction, a probe for screening was obtained by purifying the labeled product using Quick Spin Columns™ G-50 (Roche) to remove unreacted substrate. Labeling and purification were carried out according to the attached instructions.

5. Construction of cDNA Library

The cDNA used for construction of cDNA library was synthesized from the poly(A)$^+$ mRNA prepared in Example 3-4 using TimeSaver cDNA Synthesis Kit (Amersham Pharmacia Biotech). EFLCpure™ Cloned Murine Reverse Transcriptase (Amersham Pharmacia Biotech) was used as a reverse transcriptase for cDNA synthesis. The reaction temperature was 44° C.

The synthesized cDNA was ligated to the vector λZAPII (Stratagene). The ligation reaction product was subjected to packaging using Gigapack III Gold Packaging Extract (Stratagene). The phage suspension obtained by packaging as described above was used as a cDNA library.

6. Primary Screening

The phage suspension obtained by packaging was spread according to the instructions attached to ZAP-cDNA synthesis Kit (Stratagene) at a density of about $1 \times 10^5$ plaques per plate onto a 24×24-cm square-shaped Petri dish MS-12450 (Sumitomo Bakelite) in which bottom plate had been prepared and which had been incubated beforehand. The phage plaques formed on the plate were transferred to a nitrocellulose membrane NITROPLUS 2000 (Funakoshi) according to a conventional method.

The membrane was soaked in an alkali denaturation solution (0.9 M NaOH, 1.5 M NaCl) for 2 to 5 minutes followed by a neutralization solution (1.5 M Tris-HCl (pH 7.5), 1.5 M NaCl) for 2 to 5 minutes. The membrane was then washed in 6×SSC, dried and heated in a dry-heat sterilizer SP-650 (ADVANTEC) at 80° C. for 2 hours.

Prehybridization was carried out by incubating the membrane in a hybridization solution (5× Denhardt's, 4.1 mM EDTA, 0.5% SDS, 6×SSC) containing denatured salmon sperm DNA at a final concentration of 100 µg/ml at 65° C. for 2 hours.

Then, hybridization was carried out by incubating the membrane in a hybridization solution containing denatured salmon sperm DNA at a final concentration of 100 µg/ml and the probe prepared in Example 3-4 which had been heat-denatured into single strands at a final concentration of 10 ng/ml at 60° C. overnight (12 hours or longer).

After hybridization, the membrane was incubated in a washing solution (2×SSC, 0.1% SDS) at room temperature for 5 minutes to wash away unbound probe, hybridization solution and the like. The washing procedure was repeated twice.

Then, the membrane was incubated in a washing solution (0.5×SSC, 0.1% SDS), which had been incubated at 60° C. beforehand, at 60° C. for 20 minutes to dissociate nonspecifically bound probe. The washing procedure was repeated twice.

Then, the membrane was incubated in a washing solution (0.1×SSC, 0.1% SDS), which had been incubated at 60° C. beforehand, at 60° C. for 20 minutes to dissociate nonspecifically bound probe. The washing procedure was repeated twice.

Detection of digoxigenin was carried out using a color development reaction according to the instructions attached to DIG DNA Labeling and Detection Kit (Roche). The results of the detection were observed using a light box for photography LIGHT BOX NEW 5000 INVERTER (Fuji Color). The primary screening was carried out according to the above-mentioned procedure.

7. Secondary Screening

The positive phages in the primary screening were collected, and subjected to library amplification according to the method of Manabe, K., Bio Jikken Illustrated (4): Kurou Nashi No Cloning, Shujunsha (1997).

The secondary screening was carried out for plaques obtained by spreading the amplified phage suspension at a density of 50 to 100 plaques per plate onto a 9-cm Petri dish (height: 1.5 cm, diameter: 9 cm) in which bottom plate had been prepared and which had been incubated beforehand. The secondary screening was carried out in a manner similar to that as described above with respect to the primary screening.

According to the above-mentioned method, a cDNA library from leafy gametophyte was constructed, a primary screening was carried out, and positive clones were amplified. Five positive clones were isolated by screening about 1×10$^5$ plaques obtained from the amplified phage suspension. PCRs were carried out for the plaques determined to be positive in the secondary screening using two vector sequence-specific primers (T3 promoter primer (Novagen) and T7 promoter primer (Novagen)). The amplification products were subjected to electrophoresis on 1.0% agarose gel to determine the lengths of the inserted fragments.

The fragments inserted in the phage vector were subcloned into a plasmid vector by in vivo excision according to the instructions attached to ZAP-cDNA Synthesis Kits (Stratagene).

Colonies generated as a result of the in vivo excision were picked up at random, and subjected to PCRs using the above-mentioned pair of primers (T3 promoter primer and T7 promoter primer). The amplification products were subjected to electrophoresis on 1.0% agarose gel to determine the lengths of the inserted fragments.

8. Nucleotide Sequence Analysis

A plasmid having the longest cDNA insert was transferred into *Escherichia coli*. The resulting transformant was subjected to liquid culture. The plasmid was extracted using QIAGEN Plasmid Mini Kit (Qiagen). The nucleotide sequence of the inserted cDNA region was determined using the plasmid according to the primer walking method.

The determined cDNA sequence is shown in SEQ ID NO:1. A 1350-bp open reading frame (ORF, from position 79 to position 1428, including the stop codon) was found in the 1644-bp cDNA sequence. The ORF encodes a protein consisting of 449 amino acids. The amino acid sequence of the protein encoded by the ORF is shown in SEQ ID NO:8. The predicted molecular weight and isoelectric point of the protein encoded by the ORF are 49.4 kDa and 9.18, respectively.

A sequence (ATCATGG) similar to the sequence according to the Kozak rule (Kozak, M., Cell, 44:283-292 (1986)) was found in the region from position 76 to position 82 including the initiation codon.

Although the poly(A) addition signal (AATAAA) or a poly (A) tail was not found in the cDNA sequence, a sequence (TACTATT) similar to the poly(A) addition sequence reported for the CYC1 gene from the budding yeast *Saccharomyces cerevisiae* (TACATA; Proudfoot, N., Cell, 64(4): 671-674 (1991)) was found in the region from position 1579 to position 1585.

Homology searches and motif searches were carried out in order to confirm if the obtained sequence was a gene that encodes EF-1α.

Homology searches were carried out using the BLASTX 2.0.10 program in BLAST 2.0 ADVANCED BLAST SEARCH (Altschul, S. F. et al., Nucleic Acids Res., 25(17): 3389-3402 (1997) available to the public from NCBI.

Motif searches of the PROSITE motif database expasy.ch/prosite/ were carried out using the program InterPro Release 4.0 (Apweiler, R. et al., J. Biosci., 26(2):277-284 (2001) available to the public from InterPro ebi.ac.uk/interpro/.

The first hit in the homology searches using the BLASTX program (for searching amino acid sequence database using a nucleotide sequence) was observed for *Porphyra purpurea* EF-1α tef-c with the homology score of 887. The significantly low E value (an expected value of the number of hits with scores above the similarity score upon random searches of an arbitrary sequence library having the same size as the objective database) shows that the hit was not accidental. Thus, it is clear that the above-mentioned sequence determined in this Example is homologous to *Porphyra purpurea* EF-1α tef-c.

The results of amino acid motif searches using InterPro are as follows.

As a result of the searches of the PROSITE database, ATP/GTP-binding site motif A (P-loop) (PROSITE accession number PS00017) was found in the region from position 14 to position 21 (GHVDSGKS) in the amino acid sequence of SEQ ID NO:8, and GTP-binding elongation factors signature (PROSITE accession number PS00301) was found in the region from position 61 to position 76 (DKLKAERERGITI-DIA) in the amino acid sequence of SEQ ID NO:8.

Based on these results, it is considered that the DNA fragment obtained in this Example is a novel DNA fragment encoding amino acids that function as an elongation factor.

Example 4

Analyses of Expression Patterns of A1 and A2 Genes in Respective Stages of Life Cycle of *Porphyra yezoensis* Ueda using RT-PCR 1. A1 Gene (1) Primer Synthesis Primers for RT-PCR for examining the expression pattern of the A1 gene, PYEFRT1 (SEQ ID NO:4) and PYEFR1 (SEQ ID NO:5), were synthesized.

The sequence of the primer PYEFRT1 was designed by selecting a region having clearly distinct sequence based on the comparison between the sequence of the 5' untranslated region of the A1 gene represented by SEQ ID NO:1 determined in Example 3 and the sequence AV435982. The sequence AV435982 is one of the EST sequences subjected to clustering in Example 2 and belonging to the group of the A2 gene, and has the longest sequence of the 5' untranslated region.

Thus, the sequence of the primer PYEFRT1 is contained in the sequence of the 5' untranslated region of the A1 gene represented by SEQ ID NO:1 and is not homologous to the sequence of the 5' untranslated region of the A2 gene.

The sequence of the primer PYEFRT1 is a sequence in *Porphyra purpurea* elongation factor EF1-alpha (tef-c) mRNA that is also highly homologous to the EST sequences determined to belong to the group of the A2 gene upon the clustering in Example 2.

(2) RT-PCR

Total RNAs were extracted from *Porphyra yezoensis* Ueda TU-1 at the following stages according to the method as described in Example 1: 1- to 2-mm-long leafy gametophyte prior to monospore formation, 2-mm-long leafy gametophyte which had been subjected to induction of monospore release for 30 minutes, 1- to 2-cm-long leafy gametophyte, and filamentous sporophyte.

cDNA was synthesized using 200 ng of each one of the poly(A)$^+$ RNAs and RNA PCR Kit (AMV) Ver. 2.1 (Takara Shuzo). The reverse transcription reaction was carried out at 53° C. using Oligo dT-Adaptor Primer (Takara Shuzo) as a primer according to the attached instructions.

PCR was carried out using 5 ng of the resulting cDNA as a template, Gene Taq NT (Wako Pure Chemical Industries) and the two synthetic primers PYEFRT1 (SEQ ID NO:4) and PYEFR1 (SEQ ID NO:5). The PCR was carried out as follows: preheating at 94° C. for 2 minutes; 30 cycles of 94° C. for 30 seconds, 53° C. for 30 seconds and 72° C. for 1 minute and 30 seconds; and final reaction at 72° C. for 7 minutes.

As negative controls, PCRs were carried out under the same conditions using, as templates, the poly(A)$^+$ RNAs from the respective stages which had not been subjected to a reverse transcription reaction. The PCR products were subjected to electrophoresis on 1.5% agarose gel.

The results of agarose gel electrophoresis are shown in FIG. 1.

In FIG. 1, the results of agarose gel electrophoresis for the samples which had been subjected to reverse transcription reactions are shown in FIG. 1(A), and the results of agarose gel electrophoresis for the samples which had not been subjected to a reverse transcription reaction (negative controls) are shown in FIG. 1(B).

In FIGS. 1(A) and (B), the lanes represent the following:
M: 100 bp ladder marker (Takara Shuzo);
Lane 1: results obtained using, as a template, the mRNA prepared from 1- to 2-mm-long leafy gametophyte prior to monospore formation;
Lane 2: results obtained using, as a template, the mRNA prepared from 2-mm-long leafy gametophyte with monospore formation;
Lane 3: results obtained using, as a template, the mRNA prepared from 1- to 2-cm-long leafy gametophyte; and
Lane 4: results obtained using, as a template, the mRNA prepared from filamentous sporophyte.

The 391-bp amplification product was observed for each stage. Thus, it is considered that the A1 gene is highly expressed at the respective stages of the life cycle of *Porphyra yezoensis* Ueda.

2. A2 Gene (1) Primer Synthesis

A primer for RT-PCR for examining the expression pattern of the A2 gene, PYEFRT4 (SEQ ID NO:6), was designed as follows.

The sequence of the primer PYEFRT4 was designed by selecting a region having a clearly distinct sequence based on the comparison between the sequence AV435982 which belongs to the group of the A2 gene and has the longest sequence of the 5' untranslated region, and the sequence of the 5' untranslated region of the A1 gene represented by SEQ ID NO:1 determined in Example 3.

Thus, the sequence of the primer PYEFRT4 is contained in the sequence of the 5' untranslated region of the A2 gene and is not homologous to the sequence of the 5' untranslated region of the A1 gene.

The primer PYEFRT4 and the above-mentioned primer PYEFR1 (SEQ ID NO:5) were used for RT-PCR.

(2) RT-PCR

Total RNAs were extracted from *Porphyra yezoensis* Ueda TU-1 at the following stages according to the method as described in Example 1:1- to 2-mm-long leafy gametophyte prior to monospore formation, 2-mm-long leafy gametophyte which had been subjected to induction of monospore release for 30 minutes, 1- to 2-cm-long leafy gametophyte, and filamentous sporophyte.

cDNA was synthesized using 200 ng of each one of the poly(A)$^+$ RNAs and RNA PCR Kit (AMV) Ver. 2.1 (Takara Shuzo). The reverse transcription reaction was carried out at 53° C. using Oligo dT-Adaptor Primer (Takara Shuzo) as a primer according to the attached instructions.

PCR was carried out using 5 ng of the resulting cDNA as a template, Gene Taq NT (Wako Pure Chemical Industries) and the two synthetic primers PYEFRT4 (SEQ ID NO:6) and PYEFR1 (SEQ ID NO:5). The PCR was carried out as follows: preheating at 94° C. for 2 minutes; 30 cycles of 94° C. for 30 seconds, 53° C. for 30 seconds and 72° C. for 1 minute and 30 seconds; and final reaction at 72° C. for 7 minutes.

As negative controls, PCRs were carried out under the same conditions using, as templates, the poly(A)$^+$ RNAs from the respective stages which had not been subjected to a reverse transcription reaction. The PCR products were subjected to electrophoresis on 1.5% agarose gel.

Figure 2:
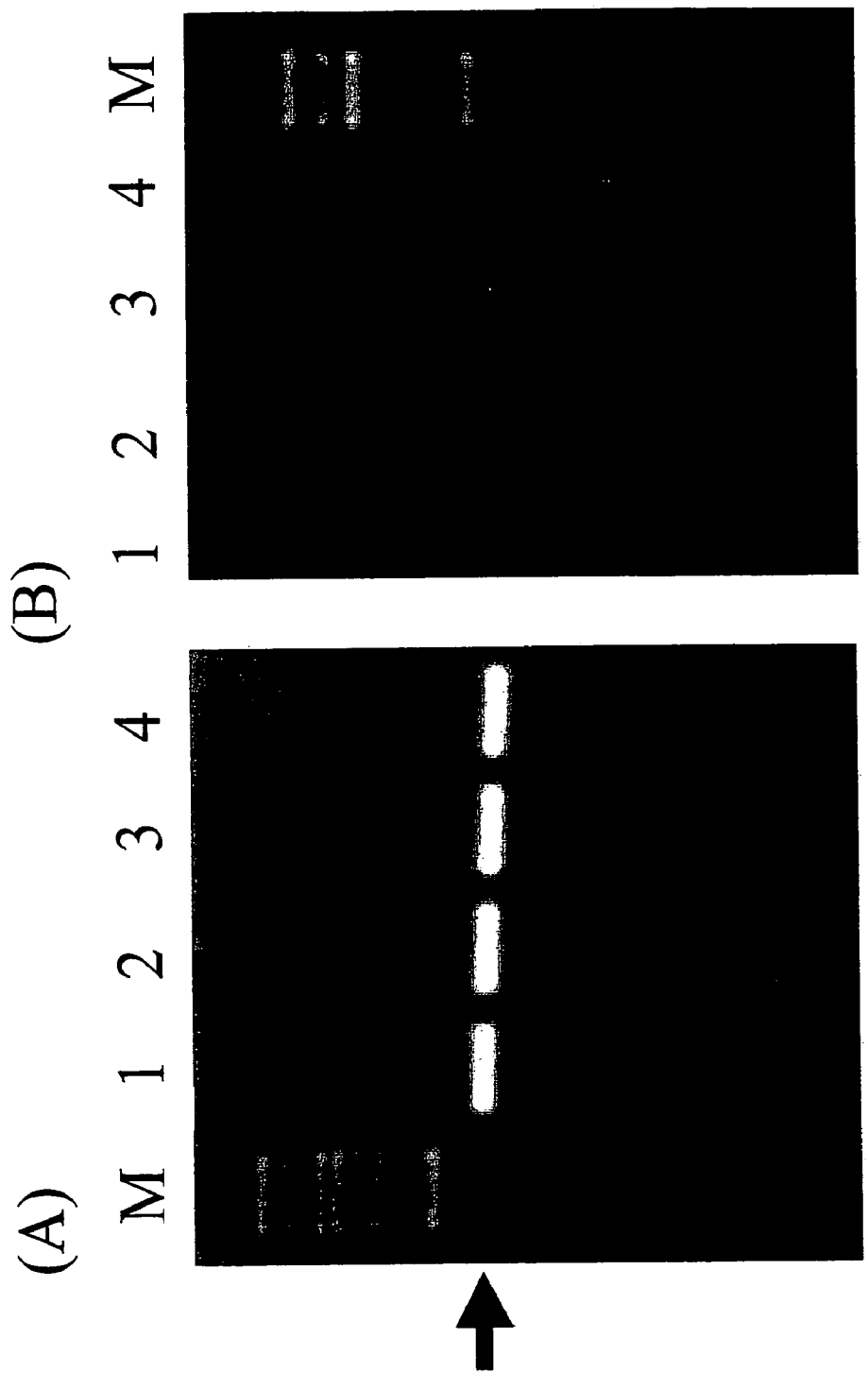
FIG. 2 illustrates the results of agarose gel electrophoresis for the A2 gene.

The results of agarose gel electrophoresis are shown in FIG. 2.

In FIG. 2, the results of agarose gel electrophoresis for the samples which had been subjected to reverse transcription reactions are shown in FIG. 2(A), and the results of agarose gel electrophoresis for the samples which had not been subjected to a reverse transcription reaction (negative controls) are shown in FIG. 2(B).

In FIGS. 2(A) and (B), the lanes represent the following:
M: 100 bp ladder marker (Takara Shuzo);
Lane 1: results obtained using, as a template, the mRNA prepared from 1- to 2-mm-long leafy gametophyte prior to monospore formation;
Lane 2: results obtained using, as a template, the mRNA prepared from 2-mm-long leafy gametophyte with monospore formation;
Lane 3: results obtained using, as a template, the mRNA prepared from 1- to 2-cm-long leafy gametophyte; and
Lane 4: results obtained using, as a template, the mRNA prepared from filamentous sporophyte.

The 369-bp amplification product was observed for each stage. Thus, it is considered that the A2 gene is highly expressed at the respective stages of the life cycle of *Porphyra yezoensis* Ueda.

Example 5

Isolation of A2 Gene from Genomic Library, Sequencing and Isolation of Promoter Sequence 1. Preparation of Genomic DNA
Genomic DNA was extracted from *Porphyra yezoensis* Ueda TU-1 using Nucleon PhytoPure, Plant and fungal DNA extraction kits (Amersham Pharmacia Biotech) according to the instructions attached to the kit with partial modification.

The procedure used for extracting genomic DNA from the alga at the stage of thallus is shown below.

After removing water using a paper towel, a cultured alga at the stage of thallus was weighed. 2.5 g of the alga was ground using a mortar and a pestle in liquid nitrogen. The ground alga was transferred, using a spoon which had been precooled in liquid nitrogen, into a 50-ml centrifuge tube containing 11.5 ml of Reagent 1 buffer attached to the kit. RNase A was added thereto at a final concentration of 20 µg/ml. The mixture was incubated at 37° C. for 30 minutes. 3.75 ml of Reagent 2 attached to the kit was then added thereto. After stirring to homogeneity, the mixture was incubated at 65° C. for 10 minutes during which the tube was pulled up and the mixture was mixed adequately three times. The tube was then incubated on ice for 20 minutes. 2 ml of chloroform was added thereto, and the resulting mixture was incubated at −20° C. for 20 minutes. 500 µl of Nucleon PhytoPure DNA extraction resin (Amersham Pharmacia Biosystems) was added thereto, and the mixture was mixed at room temperature for 10 minutes.

The mixture was centrifuged to collect an upper layer. Cesium chloride was added thereto at a final concentration of 3.2 g/3 ml and dissolved. 1/10 volume of an ethidium bromide solution (final concentration of 10 mg/ml) was further added thereto. The mixture was dispensed to ultracentrifuge tubes (12PA seal tubes, HITACHI) and centrifuged at 50,000 rpm at 15° C. for 20 hours using Hitachi ultracentrifuge 65P (HITACHI).

After centrifugation, the DNA layer was pulled from the ultracentrifuge tube while exposing it to ultraviolet light using a syringe (Terumo syringe 2.5 ml, Terumo) equipped with an injection needle (22G×1, Terumo). An equal volume of isobutanol was added to the pulled DNA layer, the mixture was stirred and centrifuged, and the lower layer was then collected (isobutanol treatment). The isobutanol treatment was repeated until the color of ethidium bromide became unobservable (two to three times).

The collected lower layer was placed in a dialysis membrane Spectra/Por 7 Membrane (Spectrum), and dialyzed against 1 l of TE buffer (10 mM Tris-HCl, 1 mM EDTA, pH7.5) at room temperature overnight. After dialysis, 1/10 volume of 3 M sodium acetate and two volumes of ethanol was added thereto and mixed. The formed precipitate was collected by centrifugation, rinsed with 75% ethanol and air-dried.

The thus obtained precipitate was dissolved in 100 µl of TE buffer. The concentration and the purity of the extracted genomic DNA were determined using a spectrophotometer Gene Quant (Amersham Pharmacia Biotech). In addition, the genomic DNA was subjected to electrophoresis on 1.0% agarose gel to confirm that it was not degraded.

2. Preparation of Probe

It was known based on the analyses in Example 2 that the A1 and A2 genes as candidates for isolating promoters are highly homologous to *Porphyra purpurea* elongation factor EF1-alpha (tef-c) mRNA (GenBank accession no. U08844).

Based on the above, elongation factor EF1-alpha genes were searched for a highly conservative motif-containing sequence for isolating genomic sequences of both of the A1 and A2 genes. Then, a forward primer PYEF1 (SEQ ID NO:7) and a reverse primer PYEFR1 (SEQ ID NO:5) were designed such that such a motif is located between the primers.

PCR was carried out using the primers, Ampli Taq Gold (PerkinElmer) and the genomic DNA from *Porphyra yezoensis* Ueda TU-1 as a template in Gene Amp PCR System 9600 (PerkinElmer). The PCR was carried out as follows: preheating at 95° C. for 10 minutes; 30 cycles of 94° C. for 1 minute, 52° C. for 1 minute and 72° C. for 2 minutes; and final reaction at 72° C. for 10 minutes. The PCR product was subjected to electrophoresis on 2.0% SeaKem GTG agarose gel (Takara Shuzo). The about 170-bp DNA fragment of interest was excised and recovered from the gel. The DNA was purified using Gene Clean II (Bio101), and ligated to a vector for TA cloning, pT7Blue (Novagen), using Ligation Kit ver. 1 (Takara Shuzo). After ligating for about 16 hours, the ligation product was used to transform *Escherichia coli* JM109 competent cells (Takara Shuzo). The transformed JM109 cells were cultured on LB agar medium containing ampicillin to form colonies.

The inserts in the plasmids harbored in the colonies were examined by colony PCR using T7 promoter primer (Novagen) which has a sequence in the vector pT7Blue and a primer M4 (Takara Shuzo). An *Escherichia coli* colony that harbors a plasmid having the DNA fragment of interest was selected.

The plasmid was extracted and purified from the selected *Escherichia coli* colony using Qiagen Plasmid Mini Kit (Qiagen) according to the instructions attached to the kit. The nucleotide sequence was determined according to the cycle sequencing method which utilizes the dideoxy method, using the plasmid as a template, Dye Termination Cycle Sequencing FS Ready Reaction Kit (PerkinElmer) and ABI Prism 310 Genetic analyzer (PerkinElmer) according to the instructions attached to the kit.

The plasmid which had been subjected to nucleotide sequence determination as described above was labeled using PCR DIG Labeling kit (Roche) according to the instructions attached to the kit to prepare a probe for screening a genomic library. After the labeling reaction, a purified labeled product was obtained by removing excess substrate using Quick Spin Columns™ G-50 (Roche). The purified labeled product was used as a probe for screening.

3. Construction of Genomic Library

The genomic DNA extracted as described in Example 5-1 was ligated to the vector λDASHII using λDASHII/BamHI Vector Kit (Stratagene) to construct a genomic library according to the instructions attached to the kit. The ligation reaction product was subjected to packaging using Gigapack III Gold Packaging Extract (Stratagene). The phage suspension was spread according to the instructions attached to the packaging extract at a density of about $1 \times 10^4$ plaques per plate onto a 90×20-mm sterile Petri dish (SH-20, Iwaki) in which bottom plate had been prepared and which had been incubated beforehand.

4. Primary Screening

The phage plaques formed on the plate were transferred to a nitrocellulose membrane NITROPLUS 2000 (Funakoshi) according to a conventional method.

The membrane was soaked in an alkali denaturation solution (1.5 M NaCl, 0.5 M NaOH) for 5 minutes followed by a neutralization solution (1.5 M NaCl, 1.5 M Tris-HCl (pH 7.5)) for 5 minutes. The membrane was then washed in 6×SSC, dried and heated in a dry-heat sterilizer SP-650 (ADVANTEC) at 80° C. for 2 hours.

Prehybridization was carried out by incubating the membrane in a hybridization solution (5×SSC, 50% formamide, 50 mM Church phosphate buffer (pH 7.0), 10% Blocking reagent (Roche), 7% SDS and 0.1% sodium N-dodecanoyl sarcosinate) containing salmon sperm DNA at a final concentration of 100 µg/ml at 65° C. for 2 hours.

Then, hybridization was carried out by incubating the membrane in a hybridization solution containing the probe which had been heat-denatured into single strands and salmon sperm DNA at a final concentration of 100 μg/ml at 50° C. overnight.

After hybridization, the membrane was incubated in a washing solution 1 (2×SSC, 0.1% SDS) at room temperature for 5 minutes to wash away unbound probe, hybridization solution and the like. The washing procedure was repeated twice.

Then, the membrane was incubated in a washing solution 2 (0.1×SSC, 0.1% SDS), which had been warmed beforehand, at 68° C. for 15 minutes to dissociate nonspecifically bound probe. The washing procedure was repeated twice.

Detection of digoxigenin was carried out using a color development reaction according to the instructions attached to DIG DNA Labeling and Detection Kit (Roche).

5. Secondary Screening

The positive phages in the primary screening were collected. A phage suspension was prepared according to a conventional method, and subjected to secondary screening.

The secondary screening was carried out in a manner similar to that as described above with respect to the primary screening except that the phage suspension was spread at a density of 50 to 100 plaques per plate onto a 90×20-mm sterile Petri dish in which bottom plate had been prepared and which had been incubated beforehand.

As a result, two positive clones No. 20 and No. 47 were obtained. The plaques determined to be positive were subjected to amplification of λ phage and extraction of λ phage DNA according to the method of Sugiura (Sugiura, M., Cloning To Sequence, Nouson Bunka Sha, Tokyo, pp. 152-156 (1989)).

6. Southern Hybridization of λ Phage DNA

The positive clones No. 20 and No. 47 obtained as a result of the secondary screening were subjected to Southern hybridization using the probe which was used for screening the genomic library.

Southern hybridization was carried out according to the method as described in Maniatis et al. (eds.), Molecular Cloning, a Laboratory Manual, Chapter 9, pp. 31-58, Cold Spring Harbor, 1989.

Specifically, the DNAs extracted from the positive clones No. 20 and No. 47 were digested with various restriction enzymes and subjected to electrophoresis on 1% agarose gel. After electrophoresis, the gel was subjected to alkali denaturation followed by neutralization. The DNAs were blotted to a nylon membrane Hybond-N (Amersham Pharmacia Biotech) overnight according to a conventional method. After blotting, the membrane was exposed to ultraviolet light (254 nm) using an ultraviolet transilluminator for 5 minutes to immobilize the DNAs onto the membrane.

Prehybridization was carried out by incubating the membrane in 20 ml of DIG-Easy-Hyb. Granules (Roche) at 42° C. for 2 hours.

Then, hybridization was carried out by incubating the membrane with the probe heat-denatured to single strands in 4 ml of the hybridization solution at 42° C. overnight.

After hybridization, the membrane was incubated in a washing solution 1 (2×SSC, 0.1% SDS) at room temperature for 5 minutes to wash away unbound probe, hybridization solution and the like. The washing procedure was repeated twice.

Then, the membrane was incubated in a washing solution 2 (0.1×SSC, 0.1% SDS), which had been warmed at 68° C. beforehand, at 68° C. for 15 minutes to dissociate nonspecifically bound probe. The washing procedure was repeated twice.

The membrane was subjected to chemiluminescence by treatment using DIG DNA Labeling and Detection Kit (Roche). After drying, it was subjected to autoradiography by exposure for 30 seconds in a cassette containing an X-ray film (Kodak).

Figure 3:
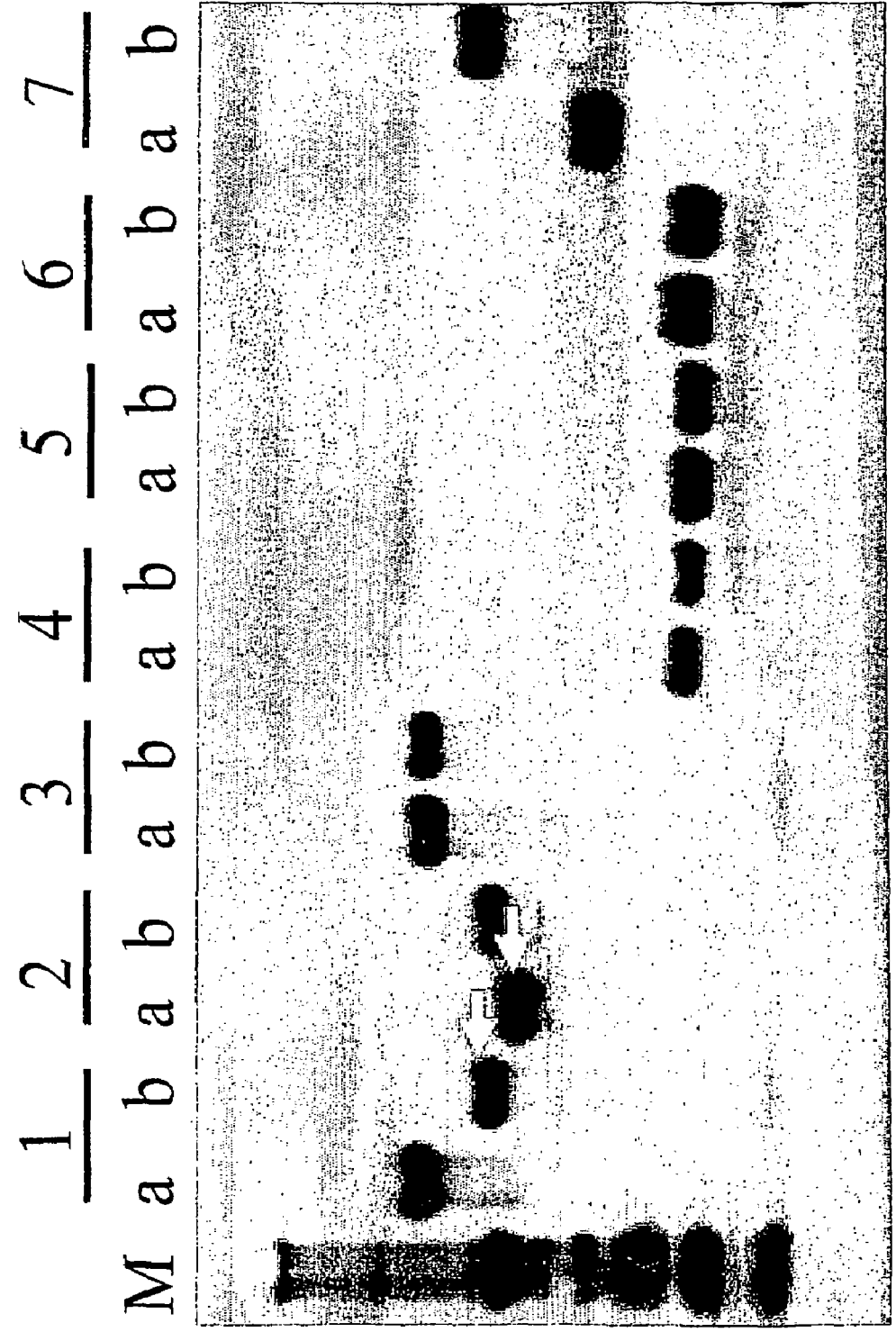
FIG. 3 illustrates the results of autoradiogram of Southern hybridization for the clone No. 20 and the clone No. 47.

The results are shown in FIG. 3.

In FIG. 3, the respective lanes represent the following. Regarding lanes 1 to 7, restriction enzyme(s) used to treat the clone No. 20 or No. 47 is(are) indicated:

M: pHY marker (Takara Shuzo);
Lane 1: HindIII;
Lane 2: HindIII and XbaI;
Lane 3: XbaI;
Lane 4: XbaI and SalI;
Lane 5: SalI;
Lane 6: SalI and EcoRI; and
Lane 7: EcoRI.

The lanes indicated with "a" represent results for the clone No. 20, while the lanes indicated with "b" represent results for the clone No. 47.

As a result, it was considered to be highly possible that the gene and the upstream region were contained in the about 4-kbp fragment of the clone No. 20 generated by double digestion with the restriction enzymes HindIII and XbaI and the about 5.5-kbp fragment of the clone No. 47 generated by digestion with the restriction enzyme HindIII.

Then, the DNA of the clone No. 20 was completely digested with the restriction enzymes HindIII and XbaI and subjected to electrophoresis on 1% agarose gel, and the about 4-kbp band was excised and recovered from the agarose gel.

Furthermore, the DNA of the clone No. 47 was completely digested with the restriction enzyme HindIII and subjected to electrophoresis on 1% agarose gel, and the about 5.5-kbp band was excised and recovered from the agarose gel.

The recovered DNA fragments were ligated with a vector plasmid pBluescriptII (ToYoBo) using TaKaRa Ligation Kit ver. 1 (Takara Shuzo). After ligating for 30 minutes, the ligation product was used to transform *Escherichia coli* JM109 competent cells (Takara Shuzo). The transformed JM109 cells were cultured on LB agar medium containing ampicillin to form colonies.

The inserts in the plasmids harbored in the colonies were examined by colony PCR using a primer RV (Takara Shuzo) which has a sequence in the vector pBluescriptII and a primer M4 (Takara Shuzo). *Escherichia coli* colonies having DNA fragments of interest were selected. The plasmids were extracted and purified from the selected *Escherichia coli* colonies using Qiagen Plasmid Mini Kit-(Qiagen) according to the instructions attached to the kit. The prepared plasmids were designated as pEF20 and pEF47, respectively.

The plasmids pEF20 and pEF47 were used to transform *Escherichia coli* JM109. The resulting transformants were designated and indicated as *Escherichia coli* JM109/pEF20 and *Escherichia coli* JM109/pEF47 (FERM P-19160). They are deposited at International Patent Organism Depositary, National Institute of Advanced Industrial Science and Technology, AIST Tsukuba Central 6, 1-1, Higashi 1-chome, Tsukuba-shi, Ibaraki 305-8566, Japan since Dec. 18, 2002 (date of original deposit) under accession number FERM P-19160, and deposited at International Patent Organism Depositary, National Institute of Advanced Industrial Science and Technology under accession number FERM BP-8285 (date of request for transmission to international depositary authority: Jan. 29, 2003)).

The nucleotide sequences were determined according to the cycle sequencing method which utilizes the dideoxy method, using the plasmids pEF20 and pEF47 as templates, Dye Termination Cycle Sequencing FS Ready Reaction Kit (PerkinElmer) and ABI Prism 310 Genetic analyzer (PerkinElmer) according to the instructions attached to the kit.

As a result, it was shown that the phage DNA of the clone No. 20 contained a sequence starting from the position 173 bp upstream of the translation initiation point of the A2 gene. Accordingly, it can be said that the promoter sequence was not contained because the upstream sequence of the genomic DNA was not contained.

As for the clone No. 47, the phage DNA contained a sequence starting from the position about 1.3-kb upstream of the translation initiation point of the A2 gene. The sequence is shown in SEQ ID NO:3.

The comparison of the determined nucleotide sequence of the clone No. 47 (SEQ ID NO:3) with the cDNA sequence (SEQ ID NO:1) and the EST sequences obtained by the clustering analyses, as well as the searches for transcription factor, coding region and intron/exon revealed that the sequence of the clone No. 47 contained a promoter sequence, an intron sequence and a terminator sequence.

Specifically, it was shown that, in the 3764-bp. DNA sequence, the sequence from position 87 to position 859 is the 5' flanking region, the sequence from position 860 to position 877 is the first exon, the sequence from position 878 to position 1331 is the first intron, the sequence from position 1332 to position 2961 is the second exon, and the sequence from position 2962 to position 3764 is the 3' flanking region. In addition, it was shown that the 5' flanking region contains a promoter sequence and the 3' flanking region contains a terminator sequence.

A sequence (ATCATGG) which is similar to the sequence according to the Kozak rule (Kozak, M., Cell, 44:283-292 (1986)) was found in the region from position 1365 to position 1371 including the initiation codon. The poly(A) addition signal for nuclear genes of higher plants, CAYTG (Joshi, C. P., Nucl. Acids Res., 15:9627-9640 (1987)) was found in the region from position 2951 to position 2965 (CATTG), and a sequence (AATAGA) which is similar to another poly(A) addition signal AATAAA was found in the region from position 2897 to position 2902.

The above-mentioned searches revealed that the sequence from position 860 to position 877 and the sequence from position 1332 to position 2961 in SEQ ID NO:3 correspond to the sequence of the cDNA for the A2 gene. The sequence is shown in SEQ ID NO:2. In the sequence, the sequence from position 65 to position 1404 is the A2 polypeptide encoding sequence (including the stop codon). The amino acid sequence of the polypeptide consisting of 499 amino acids encoded by the sequence is identical to the amino acid sequence of the polypeptide encoded by the ORF of the A1 gene (SEQ ID NO:8). Based on these results, it is considered that the DNA fragment obtained in this Example is also a DNA fragment encoding amino acids that function as an elongation factor.

Example 6

Examination of Activity of Promoter Sequence (1) Construction of Plasmid for Measuring Promoter Activity A plasmid vector for measuring a promoter activity was constructed as follows so that a promoter activity can be determined by detecting a GUS activity upon transient expression of a β-glucuronidase gene.

pBI221 (Clontech) was used as a control plasmid vector for comparison. The 35S promoter portion of the vector (a fragment from the HindIII site to the XbaI site) was replaced by the promoter sequence of the EF-1α A2 gene in pEF47 from the HindIII site to the position immediately in front of the transcription initiation site without an intron (SEQ ID NO:9) to construct a vector in which the promoter sequence is linked to the β-glucuronidase gene. Specifically, the sequence of SEQ ID NO:9 was obtained as follows. An about 0.8 kbp fragment was obtained by PCR amplification using the plasmid pEF47 as a template as well as a primer M13 RV (Takara Bio) and a primer EF47X2 (SEQ ID NO:12) which had been synthesized to have a XbaI site at the 5' end. The about 0.8-kbp fragment was completely digested with restriction enzymes HindIII and XbaI, and an about 0.8-kbp fragment was excised and purified from agarose gel after electrophoresis. The DNA fragment was ligated to a vector fragment in which the 35S promoter portion had been removed from pBI221 by complete digestion with restriction enzymes HindIII and XbaI. The ligation mixture was used to transform *E. coli* JM109. The resulting plasmid was designated as p47GUS-IL, and *E. coli* JM109 transformed with p47GUS-IL was designated as *Escherichia coli* JM109/p47GUS-IL. It was confirmed that p47GUS-IL has the promoter sequence from the HindIII site to the position immediately in front of the transcription initiation site (SEQ ID NO:9) by PCR and nucleotide sequence analysis.

The 35S promoter portion of the control plasmid vector for comparison pBI221 (a fragment from the HindIII site to the XbaI site) was replaced by a sequence including the promoter sequence, the first exon, the first intron and a portion of the second exon to the position immediately in front of ATG (from position 87 to position 1367 in SEQ ID NO:3) to construct a vector in which a sequence including the promoter sequence (SEQ ID NO:9) and the downstream first intron (SEQ ID NO:10) is linked to the β-glucuronidase gene. Specifically, the sequence including the promoter sequence, the first exon, the first intron and a portion of the second exon to the position immediately in front of ATG (from position 87 to position 1367 in SEQ ID NO:3) was obtained as follows. An about 1.3 kbp fragment was obtained by PCR amplification using the plasmid pEF47 as a template as well as a primer M13 RV (Takara Bio) and a primer EF47X (SEQ ID NO:13) which had been synthesized to have a XbaI site at the 5' end. The about 1.3-kbp fragment was completely digested with restriction enzymes HindIII and XbaI, and an about 1.3-kbp fragment was excised and purified from agarose gel after electrophoresis. The DNA fragment was ligated to a vector fragment in which the 35S promoter portion had been removed from pBI221 by complete digestion with restriction enzymes HindIII and XbaI. The ligation mixture was used to transform *E. coli* JM109. The resulting plasmid was designated as p47GUS, and *E. coli* JM109 transformed with p47GUS was designated as *Escherichia coli* JM109/p47GUS. It was confirmed that p47GUS has a sequence from position 87 to position 1367 in SEQ ID NO:3 by PCR and nucleotide sequence analysis.

(2) Determination of Promoter Activity

Promoter activities were determined by transferring the vectors pBI221, p47GUS-IL and p47GUS into *Porphyra yezoensis* Ueda TU-1 by means of a particle gun, and conducting histochemical assays for GUS activity due to transient expression of the β-glucuronidase gene in which the presence of blue indigotin dye accumulated in cells is observed using an erecting microscope.

The procedure used for coating gold particles with DNA for transferring the vectors into the cells is described below. 60 mg of gold particles were weighed in a 1.5-ml microfuge tube. 1 ml of freshly prepared 70% ethanol was added thereto.

The tube was stirred for 5 minutes using a tube mixer VORTEX GENIE 2 (Scientific Industries), and allowed to stand at room temperature for 15 minutes. The tube was centrifuged in a desktop centrifuge Chibitan (Millipore) for 5 seconds and the supernatant was removed. 1 ml of sterile water was added thereto. After stirring using the tube mixer for 1 minute, the tube was allowed to stand for 1 minute to sediment the gold particles. The tube was centrifuged in a desktop centrifuge for 2 seconds and the supernatant was removed. This procedure was repeated three times. 50% glycerol was added thereto such that the final concentration of the gold particle became 60 mg/ml. The tube was vigorously stirred using the tube mixer for 5 minutes in order to resuspend the gold particles in 50% glycerol (60 mg/ml) and disrupt aggregates. 50 µl of the suspension (containing about 3 mg of the gold particle) was transferred to a 1.5-ml microfuge tube. 10 µl of DNA (1 µg/µl), 50 µl of 2.5 M $CaCl_2$ and 20 µl of 0.1 M spermidine were added thereto while vigorously stirring the tube using the tube mixer, and the stirring was further continued for three minutes. The tube was allowed to stand for 1 minute to sediment the gold particles and centrifuged in a desktop centrifuge for 2 seconds, and the supernatant was removed. 140 µl of 70% ethanol was added thereto such that the pellet was not disturbed, and the supernatant was removed. Then, 140 µl of 100% ethanol was added thereto such that the pellet was not disturbed, and the supernatant was removed. 48 µl of 100% ethanol was added thereto and mixed. 8 µl of the suspension was used for one round of transfer.

A cultured single algal leafy gametophyte of *Porphyra yezoensis* Ueda TU-1 was cultured with circulation at 15° C. under short-day conditions with 10 hours in the light (light volume of 80 µE/m²/s; cool white fluorescent lamp) and 14 hours in the dark in a 2 L simplified culture vessel (Fujimori Kogyo) containing the ESL medium with aeration (air sterilized by filtration through 0.2-µm filter, 0.25 l/min). The medium was exchanged every seven days. The leafy gametophyte was cut into pieces of about 2 cm², and put on a ¼ piece of Glass Microfibre GF/C (47 mm, Whatman) while spreading in the ESL medium. They were placed on a Buechner funnel (for 70-mm filter paper, MT) mounted with a filter paper (90 mm, Whatman) moistened with the ESL medium, and subjected to aspiration using a filtering flask and an aspirator for adsorption while removing excess water. The adsorbed leafy gametophyte pieces were placed on the ESL agar medium, and the DNA-coated gold particles were transferred thereinto using a particle gun GIE-III (Tanaka) according to the attached instructions. The shooting conditions were as follows: the distance between the outlet and the sample: 7 to 9 cm; shooting pressure: 0.5 to 6.0 kgf/cm²; shooting time: 0.015 second. Three samples were subjected to the transfer for each condition.

After transfer, the samples were pealed from Glass Microfibre, classified according to the transferred vectors and the outlet-sample distance conditions, and cultured for 2 days in simplified culture vessels at 15° C. under long-day conditions with 14 hours in the light and 10 hours in the dark. Then, fixation using a fixation solution (2% paraformaldehyde, 0.1 M Na-phosphate (pH 7.0), 1 mM EDTA, 1.5 M D-sorbitol) for 1 hour and three rounds of washing in a washing solution (0.1 M Na-phosphate (pH 7.0), 1.5 M D-sorbitol were carried out. X-Gluc solution (2 mM X-Gluc (5-bromo-4-chloro-3-indolyl-β-D-glucuronide, 50 mM Na-phosphate (pH 7.0), 10 mM EDTA, 0.5 mM $K_4Fe(CN)_6$, 0.5 mM $K_3Fe(CN)_6$, 1.5 M D-sorbitol, 0.5% Triton X-100) was added thereto such that the cells or the tissues were fully soaked. The mixture was incubated overnight in a sealed suitable container in an incubator MIR-253 (Sanyo) at 37° C. The β-glucuronidase activity (GUS activity), which represents the promoter activity, was determined based on the presence of blue indigotin dye accumulated in cells observed using an erecting microscope.

As a result, among the samples into which the vector pBI221 had been transferred, GUS activities were observed for two samples obtained with the outlet-sample distance of 9 cm. As to the vector p47GUS-IL, GUS activities were observed for two samples, one obtained with the outlet-sample distance of 8 cm and the other obtained with the outlet-sample distance of 9 cm. Thus, it was demonstrated that the promoter in this vector (SEQ ID NO:9) has a promoter activity.

As to the vector p47GUS, GUS activities were observed for seven samples, one obtained with the outlet-sample distance of 7 cm, three obtained with the outlet-sample distance of 8 cm, and three obtained with the outlet-sample distance of 9 cm.

Figure 4:
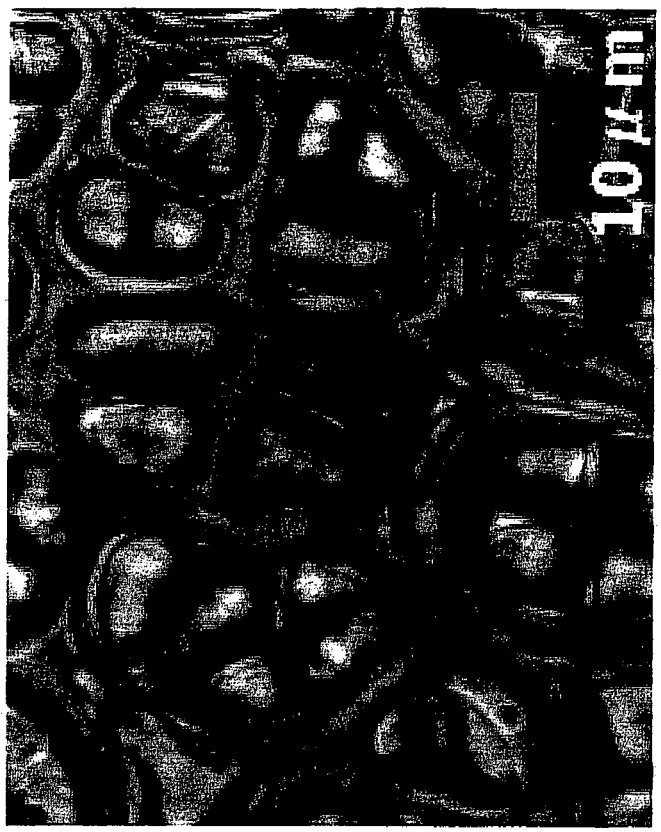
FIG. 4 illustrates accumulation of indigotin dye in cells one week after the transfer of the vector p47GUS, A: before decolorization; B: seven days after decolorization.
Figure 4:
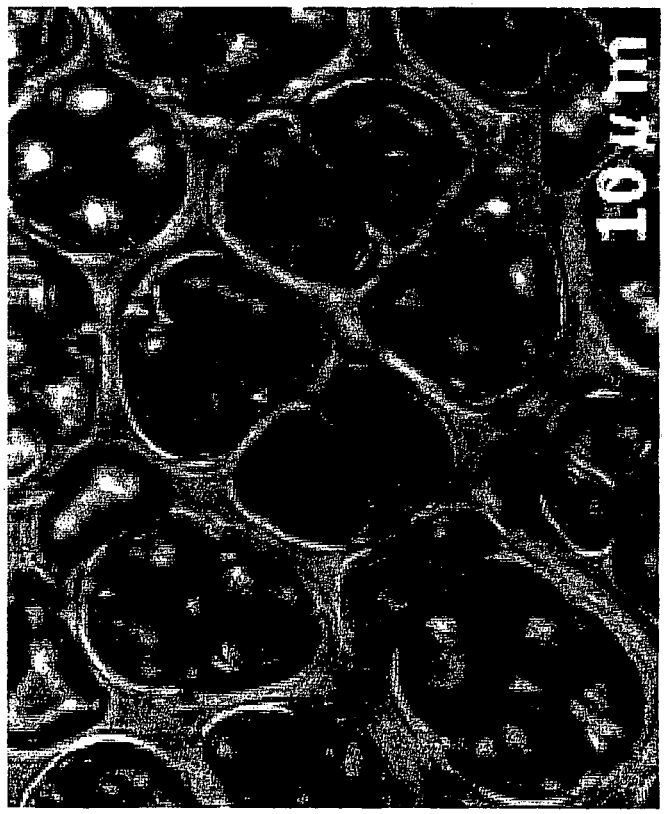

The samples for which GUS activities were observed were subjected to decolorization of the dye from the cells. As a result, the accumulated blue indigotin dye remained in the sample obtained with the outlet-sample distance of 9 cm and one of the 12 pressure conditions used for the transient transfer of the vector p47GUS (0.5 to 6.0 Kg/cm²) even after about one week (FIG. 4). In FIG. 4, "A" represents results obtained before decolorization and "B" represents results obtained seven days after decolorization. Thus, it is considered that more efficient gene expression and very high expression induction can be made possible by including the first intron (SEQ ID NO:10) downstream of the promoter (SEQ ID NO:9) in the vector.

INDUSTRIAL APPLICABILITY

According to the present invention, a promoter derived from an alga is provided for the first time. Then, gene expression in an alga utilizing the promoter has become possible. According to the present invention, a terminator and an intron derived from an alga are provided for the first time. Utilizing them, increase in gene expression efficiency in an alga has become possible. Thus, the present invention enables not only production of useful substances in algae using genetic engineering techniques, but also breeding of algae using genetic engineering techniques.

Furthermore, the present invention provides a gene for a novel elongation factor from an alga. Utilizing the gene, production of an elongation factor from an alga using genetic engineering techniques has become possible.

Sequence Listing Free Text

SEQ ID No:1: cDNA sequence of A1 gene
SEQ ID No:2: cDNA sequence of A2 gene
SEQ ID No:3: Genomic DNA sequence of A2 gene
SEQ ID No:4: Primer PYEFRT1
SEQ ID No:5: Primer PYEFR1
SEQ ID No:6: Primer PYEFRT4
SEQ ID No:7: Primer PYEF1
SEQ ID No:8: Amino acid sequence of A1
SEQ ID No:9: Promotor region of A2 gene
SEQ ID No:10: Intron 1 of A2 gene
SEQ ID No:11: Terminator region of A2 gene
SEQ ID No:12: Primer EF47X2
SEQ ID No:13: Primer EF47X

The invention claimed is:

1. An isolated DNA that exhibits a promoter activity in an alga and has the nucleotide sequence of SEQ ID NO:9.

2. A recombinant DNA in which an objective gene is operably linked to the isolated DNA of claim 1.

3. The DNA according to claim 2, wherein the objective gene is a nucleic acid selected from the group consisting of a protein-encoding nucleic acid, an antisense nucleic acid-encoding nucleic acid, and a ribozyme-encoding nucleic acid.

4. A vector containing the isolated DNA of claim 1.

5. The vector according to claim 4, which is a plasmid vector or a virus vector.

6. An alga into which the DNA defined by any one of claims 2 and 3 is transferred, or that is transformed with the vector defined by any one of claims 4 and 5.

* * * * *

SEQUENCE LISTING

<160> NUMBER OF SEQ ID NOS: 13

<210> SEQ ID NO 1
<211> LENGTH: 1644
<212> TYPE: DNA
<213> ORGANISM: Porphyra yezoensis Ueda
<220> FEATURE:
<221> NAME/KEY: misc_feature
<223> OTHER INFORMATION: cDNA sequence of A1 gene

<400> SEQUENCE: 1

| | | | | | | |
|---|---|---|---|---|---|---|
| caccatcccg | ctcgacctac | cggttgttgc | ccagtcccgt | cccgcgcgga | gtgagagcag | 60 |
| cccacctagt | ctctcatcat | ggggaaggag | aagcagcatg | tgtccattgt | ggtcattggc | 120 |
| cacgtcgact | ctggcaagtc | gacgaccacc | ggccatctga | tctacaagtg | cgggggtatc | 180 |
| gagaagcgcg | cgattgagaa | gttcgagaag | gaggctgctg | agatgggcaa | gggctcgttc | 240 |
| aagtacgcgt | gggtgctgga | caaactgaag | gccgagcgcg | agcgcggtat | caccattgac | 300 |
| attgctctgt | ggaagttcga | gacggagaag | tacagcttca | ctatcattga | cgccccgggt | 360 |
| caccgtgact | tcatcaagaa | catgatcacg | ggcacgtcgc | aggcggatct | ggccatcctg | 420 |
| gtcattgctt | cgccgccggg | cgagtttgag | gcgggtatct | cccagaacgg | gcagacccgc | 480 |
| gagcacgcgc | tgctggccta | caccctgggc | gtcaagcaga | tgattgtggc | ttgcaacaag | 540 |
| atggacgaca | agaacgtcaa | ctggtcgcag | gaccgctacg | aggaggtgtc | caaggagatg | 600 |
| gacctgtacc | tgaagaaggt | cgggtacaac | cccgccaagt | gcccaaggt | gccgacgtcg | 660 |
| ggctggacgg | gtgagaacct | gttcgagagg | accgataaga | cgcacgccct | cggcaagtgg | 720 |
| tacaagggcc | cgtgcctgct | ggaggctctg | gacaactgcg | acccgccgaa | gcgcccggtt | 780 |
| gacaagccgc | tgcgcctgcc | cctccaggac | gtctacaaga | tcggcggcat | tggcacagtg | 840 |
| ccggtgggcc | gtgtggagac | tgggctcatc | aagcccggca | tggtcgtgac | gtttgcgccc | 900 |
| tcgggcctgt | cgactgaggt | gaagtcggtc | gagatgcacc | acgaggcgct | gccccaggcc | 960 |
| ggccccggcg | acaacgttgg | cttcaacgtc | aagaacgtgt | cggtcaagga | cctgaagcgc | 1020 |
| ggctacgtgt | gcggtgactc | gaagaacgac | ccgccgaagg | ggtgcgcttc | gttcaacgcc | 1080 |
| caggtcatca | tcctgaacca | ccctggtgag | atccacgctg | gctacgcgcc | ggtgctggat | 1140 |
| tgccacacgg | cgcacattgc | gtgcaagttc | tcggagctga | tcctgaagat | ggaccgccgc | 1200 |
| tcgggcaaga | agctggagga | cacgcccaag | atgatcaagt | ccggtgacgc | tgctatggtg | 1260 |
| aagatggttg | cctccaagcc | gatgtgcgtg | gaggccttca | cccagtaccc | gccgctgggc | 1320 |
| cgctttgccg | tgcgtgacat | gcgccagacg | gtcgctgttg | gtgtcatcaa | gtcggtggag | 1380 |
| aagaaggagg | ttgagggcaa | gatgaccaag | tcggcggcca | agaaatagca | gccaattgtg | 1440 |
| ctcgcttcgg | cgtcgtgtat | ggcatcgtgg | gtggacttgt | ttttgcggt | gcgatctagt | 1500 |
| cacgcgctct | tacgcctcgc | gtgtggggtc | ctggcggtgg | tgcgtggcga | ctgtcggtct | 1560 |
| cccgtgatgg | accgtttgta | ctattcgacc | cttgcgaagg | ggagaatagg | agtgtagttt | 1620 |
| accctcttgt | tttgtatctt | tttg | | | | 1644 |

<210> SEQ ID NO 2
<211> LENGTH: 1648
<212> TYPE: DNA
<213> ORGANISM: Porphyra yezoensis Ueda

<400> SEQUENCE: 2

-continued

```
ccgtcttccc cgccgattac gtcttgagtt tacctgttca cctagccttt catcatgggg      60
aaggagaagc agcatgtgtc cattgtggtc attggccacg tcgactctgg caagtcgacg     120
accaccggcc atctgatcta caagtgcggg ggtatcgaga agcgcgcgat tgagaagttc     180
gagaaggagg ctgctgagat gggcaagggc tcgttcaagt acgcgtgggt gctggacaaa     240
ctgaaggccg agcgcgagcg cggtatcacc attgatattg ctctgtggaa gttcgagacg     300
gagaagtaca gcttcactat cattgacgcc ccgggtcacc gtgacttcat caagaacatg     360
atcacgggca cgtcgcaggc ggatctggcc atcctggtca ttgcttcgcc gccgggcgag     420
tttgaggcgg gtatctccca gaacgggcag acccgcgagc acgcgctgct ggcctacacc     480
ctgggcgtca agcagatgat tgtggcttgc aacaagatgg acgacaagaa cgtcaactgg     540
tcgcaggacc gctacgagga ggtgtccaag gagatggacc tgtacctgaa gaaggtcggg     600
tacaaccccg ccaaggtgcc caaggtgccg acgtcgggct ggacgggtga gaacctgttc     660
gagaggaccc ataagacgca cgccctcggt aagtggtaca agggcccgtg cctgctggag     720
gctctggaca actgcgaccc gccgaagcgc ccggttgaca agccgctgcg cttgcccctc     780
caggatgtct ataagatcgg cggcattggc acagtgccgg tgggccgtgt ggagactggg     840
ctcatcaagc ccggcatggt cgtgacgttt gcgccctcgg gcctgtcgac tgaggtgaag     900
tcggtcgaga tgcaccacga ggcgctgccc caggccggcc ccggcgacaa cgttggcttc     960
aacgtcaaga acgtgtcggt caaggacctg aagcgcggct acgtgtgcgg tgactcgaag    1020
aacgacccgc cgaaggggtg cgcttcgttc aacgcccagg tcatcatcct gaaccacccc    1080
ggtgagatcc acgccggcta cgccgcggtg ctggactgcc acacggcgca cattgcgtgc    1140
aagttctcgg agctgatcct gaagatggac cgccgctcag gcaagaagct ggaggacacg    1200
cccaagatga tcaagtccgg tgacgctgct atggtgaaga tggttgcctc caagccgatg    1260
tgcgtggagg ccttcaccca gtacccgccg ctgggccgct tgccgtgcg tgacatgcgc    1320 cagacggtcg ctgttggtgt catcaagtcg gtggagaaga aggaggttga gggcaagatg    1380
accaagtcgg cggccaagaa atagcagcca acccatccgg ctgtgaggtc gctggtggcc    1440
tcgctcgctg cagaccagat gcgagtcaac caggagcgcg ttatcgcgct cttcgttgtc    1500
aacgctgtca tgactgtcgc gaaggatggg tgccggtccg cagcagtcga ccgcctctac    1560
tactcgacgc tcgcgaaagg gagaatagaa atgtagcgtg cttgtcttgc ttttgctagg    1620
gtgtttcttg aggcttgcat tgtctcgc                                       1648
```

<210> SEQ ID NO 3
<211> LENGTH: 3764
<212> TYPE: DNA
<213> ORGANISM: Porphyra yezoensis Ueda
<220> FEATURE:
<221> NAME/KEY: misc_feature
<223> OTHER INFORMATION: Genomic sequence of A2 gene
<220> FEATURE:
<221> NAME/KEY: misc_feature
<222> LOCATION: (3741)..(3742)
<223> OTHER INFORMATION: n is a, c, g, or t

<400> SEQUENCE: 3

```
gactgattcg ccagcgcgca attaccctc actaaaggga acaaaagctg ggtaccgggc       60
cccccctcga ggtcgacggt atcgataagc ttcgctgcca ggctctccat cagcgacttg     120
cggtcggtgc tgtttgggga ccggcgggaa gcgcaccaga atgtgggggg agacaggcag     180
ggctcagaga cacgagtgga gagcattgat cagtaacagt cgcacgtcag actgggtctg     240
```

-continued

```
cgtggggcca cgaaagcgca aaaatgggcc tagcaggcgc cgtcaacctt ctcaagctca    300
gagcgccgcc aggctgcaca cccccgaggc gacggccagt agcacctgcg ccacggagac    360
accgtctcct gctaacatac ggttgttcgt ccgccatcga gaacagctag gtacagaata    420
ccacgaggaa gggaagaaaa gccttgaatg gcaaagggtg gtcgaaggca agccagagag    480
ggacgttcta catgcaccaa agccagtagg agcgcactac gcggtaagcg gtcgccgaaa    540
gagggggggc gacccacgct cgtcactgca ggttgtattg tgccggtccg caactgccac    600
tggcggtgtt tgtcaagcgg ccaccacgag tctcgagggc tcagcaattg caccgctggc    660
acgcagaatg tggccttccc cgagtttaca gtggtccttt tccccgaaag catccctaaa    720
aaaaggaatt gagcgacggc gacgccgacc gacgtccgcg gcggcggcca caggcgaggg    780
acggaggacc accggccttt taaatgggcg tcgaagacca cgtgctcggc acaccacccc    840
gtcgacatcg ctatcgtacc cgtcttcccc gccgattgta cgttttttttt atcctcccgc    900
cgctcagcct cccgttactc ccgcgcatac gtgtgggcgt gggtgacctg ggtgcgcgca    960
tgggcgtttc cttccctgcc ggtgtgccga gtaacggctg gctggtttgg gtggctcaac   1020
ctttgtggga gagggtcgca cctttgcacc agctgggggtg gtttgccgta tgaccaacag   1080
gctcggcaat acggatcatt gtccgactac tggcgtcggg gtgcattcag gcatgcggac   1140
actggaagaa gatcagtggt ggcgccccgg cagttgtcgt tggtcctctg gtatatgcgt   1200
tcgacagttg atcatctctt ctggtgaaga ttgctgacgc tctccggtct cttgcactgt   1260
tgtggtgatt gtttgggcgc atgttctatt cttctgatct gatcgttcct actgtcgacg   1320
gcggatcaca gacgtcttga gtttacctgt tcacctagcc tttcatcatg gggaaggaga   1380
agcagcatgt gtccattgtg gtcattggcc acgtcgactc tggcaagtcg acgaccaccg   1440
gccatctgat ctacaagtgc gggggtatcg agaagcgcgc gattgagaag ttcgagaagg   1500
aggctgctga gatgggcaag ggctcgttca agtacgcgtg ggtgctggac aaactgaagg   1560
ccgagcgcga gcgcggtatc accattgata ttgctctgtg gaagttcgag acggagaagt   1620
acagcttcac tatcattgac gccccgggtc accgtgactt catcaagaac atgatcacgg   1680
gcacgtcgca ggcggatctg gccatcctgg tcattgcttc gccgccgggc gagtttgagg   1740
cgggtatctc ccagaacggg cagacccgcg agcacgcgct gctggcctac accctgggcg   1800
tcaagcagat gattgtggct tgcaacaaga tggacgacaa gaacgtcaac tggtcgcagg   1860
accgctacga ggaggtgtcc aaggagatgg acctgtacct gaagaaggtc gggtacaacc   1920
ccgccaaggt gcccaaggtg ccgacgtcgg gctggacggg tgagaacctg ttcgagagga   1980
ccgataagac gcacgccctc ggtaagtggt acaagggccc gtgcctgctg gaggctctgg   2040
acaactgcga cccgccgaag cgcccggttg acaagccgct gcgcttgccc ctccaggatg   2100
tctataagat cggcggcatt ggcacagtgc cggtgggccg tgtggagact gggctcatca   2160
agcccggcat ggtcgtgacg tttgcgccct cgggcctgtc gactgaggtg aagtcggtcg   2220
agatgcacca cgaggcgctg ccccaggccg gccccggcga caacgttggc ttcaacgtca   2280
agaacgtgtc ggtcaaggac ctgaagcgcg gctacgtgtg cggtgactcg aagaacgacc   2340
cgccgaaggg gtgcgcttcg ttcaacgccc aggtcatcat cctgaaccac cctggtgaga   2400
tccacgccgg ctacgcgccg gtgctggact gccacacggc gcacattgcg tgcaagttct   2460
cggagctgat cctgaagatg gaccgccgct caggcaagaa gctggaggac acgcccaaga   2520
tgatcaagtc cggtgacgct gctatggtga agatggttgc ctccaagccg atgtgcgtgg   2580
aggccttcac ccagtacccg ccgctgggcc gctttgccgt gcgtgacatg cgccagacgg   2640
```

-continued

```
tcgctgttgg tgtcatcaag tcggtggaga agaaggaggt tgagggcaag atgaccaagt    2700
cggcggccaa gaaatagcag ccaacccatc cggctgtgag gtcgctggtg gcctcgctcg    2760
ctgcagacca gatgcgagtc aaccaggagc gcgttatcgc gctcttcgtt gtcaacgctg    2820
tcatgactgt cgcgaaggat gggtgccggt ccgcagcagt cgaccgcctc tactactcga    2880
cgctcgcgaa agggagaata gaaatgtagc gtgcttgtct tgcttttgct agggtgtttc    2940
ttgaggcttg cattgtctcg cgaaaaaaac attgctttcg tacgccactg gtcaacatgg    3000
atattgaacg aggacggtga agactccgtg gggcgccagg aatgcgtgat cagactttct    3060
tgacagctta gctgctttgc aagaggggcg cccatcctgc cccagagccg gtcaagagac    3120
ttaccgctgg cgccgcgcat gaccagcagc gacgcgttaa gacgaggaca cgtccagcca    3180
catggacaag aaaacaaaaa aacaaaacca agaaacgttt gggcaactgg acaaaaacgt    3240
ggccacagca gtccaagatg atcgctccgc aacagacgtc catcgcggca atcttgccgg    3300
agcggccacc ccaaacgtgc catgagaaac aaatcaccac cacaaaaaag agaattccaa    3360
cagagcctga ccatcgacac gcggggggggg gggcagcaac gcgctcgttc ccggggggctc    3420 acccccgccc actgactcca gcacggagcc cgtgggccaa ccactacctg cgcagcggct    3480
ggaatggggg gtccatgttc acgcacaggc cctggccaag acccagctcc atcattggca    3540
aagccagccc caagtcaagg tcgacgtcgg cgttcgcgtt cgcgtctgcg tcggcgtcag    3600
catcagcgtc cgaattgtca gccatgccgg ccctgccccc gtagtccaca tcacgaatgc    3660
tcgtcgggct gtgccacccc cactgtgcgc tgctctctcc ggattcatcc cgtgtccatg    3720
acgctgcctc cattcgagga nnagactgtc gccagcaaca ccgg                     3764
```

<210> SEQ ID NO 4
<211> LENGTH: 19
<212> TYPE: DNA
<213> ORGANISM: Artificial
<220> FEATURE:
<223> OTHER INFORMATION: Primer PYEFRT1

<400> SEQUENCE: 4
tcgacctacc ggttgttgc                                                    19

<210> SEQ ID NO 5
<211> LENGTH: 21
<212> TYPE: DNA
<213> ORGANISM: Artificial
<220> FEATURE:
<223> OTHER INFORMATION: Primer PYEFR1

<400> SEQUENCE: 5
ctgcgaggtg cccgtgatca t                                                21

<210> SEQ ID NO 6
<211> LENGTH: 19
<212> TYPE: DNA
<213> ORGANISM: Artificial
<220> FEATURE:
<223> OTHER INFORMATION: Primer PYEFRT4

<400> SEQUENCE: 6
ccgccgatta cgtcttgag                                                    19

<210> SEQ ID NO 7
<211> LENGTH: 21
<212> TYPE: DNA

<213> ORGANISM: Artificial
<220> FEATURE:
<223> OTHER INFORMATION: Primer PYEF1

<400> SEQUENCE: 7
ggctccttca agtacgcgtg g                                              21

<210> SEQ ID NO 8
<211> LENGTH: 449
<212> TYPE: PRT
<213> ORGANISM: Porphyra yezoensis Ueda

<400> SEQUENCE: 8

Met Gly Lys Glu Lys Gln His Val Ser Ile Val Val Ile Gly His Val
1               5                   10                  15

Asp Ser Gly Lys Ser Thr Thr Thr Gly His Leu Ile Tyr Lys Cys Gly
            20                  25                  30

Gly Ile Glu Lys Arg Ala Ile Glu Lys Phe Glu Lys Glu Ala Ala Glu
        35                  40                  45

Met Gly Lys Gly Ser Phe Lys Tyr Ala Trp Val Leu Asp Lys Leu Lys
    50                  55                  60

Ala Glu Arg Glu Arg Gly Ile Thr Ile Asp Ile Ala Leu Trp Lys Phe
65              70                  75                  80

Glu Thr Glu Lys Tyr Ser Phe Thr Ile Ile Asp Ala Pro Gly His Arg
                85                  90                  95

Asp Phe Ile Lys Asn Met Ile Thr Gly Thr Ser Gln Ala Asp Leu Ala
            100                 105                 110

Ile Leu Val Ile Ala Ser Pro Pro Gly Glu Phe Glu Ala Gly Ile Ser
        115                 120                 125

Gln Asn Gly Gln Thr Arg Glu His Ala Leu Leu Ala Tyr Thr Leu Gly
    130                 135                 140

Val Lys Gln Met Ile Val Ala Cys Asn Lys Met Asp Asp Lys Asn Val
145                 150                 155                 160

Asn Trp Ser Gln Asp Arg Tyr Glu Glu Val Ser Lys Glu Met Asp Leu
                165                 170                 175

Tyr Leu Lys Lys Val Gly Tyr Asn Pro Ala Lys Val Pro Lys Val Pro
            180                 185                 190

Thr Ser Gly Trp Thr Gly Glu Asn Leu Phe Glu Arg Thr Asp Lys Thr
        195                 200                 205

His Ala Leu Gly Lys Trp Tyr Lys Gly Pro Cys Leu Leu Glu Ala Leu
    210                 215                 220

Asp Asn Cys Asp Pro Pro Lys Arg Pro Val Asp Lys Pro Leu Arg Leu
225                 230                 235                 240

Pro Leu Gln Asp Val Tyr Lys Ile Gly Gly Ile Gly Thr Val Pro Val
                245                 250                 255

Gly Arg Val Glu Thr Gly Leu Ile Lys Pro Gly Met Val Val Thr Phe
            260                 265                 270

Ala Pro Ser Gly Leu Ser Thr Glu Val Lys Ser Val Glu Met His His
        275                 280                 285

Glu Ala Leu Pro Gln Ala Gly Pro Gly Asp Asn Val Gly Phe Asn Val
    290                 295                 300

Lys Asn Val Ser Val Lys Asp Leu Lys Arg Gly Tyr Val Cys Gly Asp
305                 310                 315                 320

Ser Lys Asn Asp Pro Pro Lys Gly Cys Ala Ser Phe Asn Ala Gln Val
                325                 330                 335

```
Ile Ile Leu Asn His Pro Gly Glu Ile His Ala Gly Tyr Ala Pro Val
                340                 345                 350

Leu Asp Cys His Thr Ala His Ile Ala Cys Lys Phe Ser Glu Leu Ile
            355                 360                 365

Leu Lys Met Asp Arg Arg Ser Gly Lys Lys Leu Glu Asp Thr Pro Lys
        370                 375                 380

Met Ile Lys Ser Gly Asp Ala Ala Met Val Lys Met Val Ala Ser Lys
385                 390                 395                 400

Pro Met Cys Val Glu Ala Phe Thr Gln Tyr Pro Pro Leu Gly Arg Phe
                405                 410                 415

Ala Val Arg Asp Met Arg Gln Thr Val Ala Val Gly Val Ile Lys Ser
            420                 425                 430

Val Glu Lys Lys Glu Val Glu Gly Lys Met Thr Lys Ser Ala Ala Lys
        435                 440                 445

Lys

<210> SEQ ID NO 9
<211> LENGTH: 773
<212> TYPE: DNA
<213> ORGANISM: Porphyra yezoensis Ueda

<400> SEQUENCE: 9
aagcttcgct gccaggctct ccatcagcga cttgcggtcg gtgctgtttg gggaccggcg      60
ggaagcgcac cagaatgtgg ggggagacag gcagggctca gagacacgag tggagagcat    120
tgatcagtaa cagtcgcacg tcagactggg tctgcgtggg gccacgaaag cgcaaaaatg    180
ggcctagcag gcgccgtcaa ccttctcaag ctcagagcgc cgccaggctg cacaccccccg   240 aggcgacggc cagtagcacc tgcgccacgg agacaccgtc tcctgctaac atacggttgt    300
tcgtccgcca tcgagaacag ctaggtacag aataccacga ggaagggaag aaaagccttg    360
aatggcaaag ggtggtcgaa ggcaagccag agagggacgt tctacatgca ccaaagccag    420
taggagcgca ctacgcggta agcggtcgcc gaaagagggg gggcgaccca cgctcgtcac    480
tgcaggttgt attgtgccgg tccgcaactg ccactggcgg tgtttgtcaa gcggccacca    540
cgagtctcga gggctcagca attgcaccgc tggcacgcag aatgtggcct tccccgagtt    600
tacagtggtc cttttccccg aaagcatccc taaaaaaagg aattgagcga cggcgacgcc    660
gaccgacgtc cgcggcggcg gccacaggcg agggacggag gaccaccggc cttttaaatg    720
ggcgtcgaag accacgtgct cggcacacca ccccgtcgac atcgctatcg tac           773

<210> SEQ ID NO 10
<211> LENGTH: 454
<212> TYPE: DNA
<213> ORGANISM: Porphyra yezoensis Ueda
<220> FEATURE:
<221> NAME/KEY: misc_feature
<223> OTHER INFORMATION: Intron 1 of A2 gene

<400> SEQUENCE: 10
gtacgttttt tttatcctcc cgccgctcag cctcccgtta ctcccgcgca tacgtgtggg     60
cgtgggtgac ctgggtgcgc gcatgggcgt ttccttccct gccggtgtgc cgagtaacgg    120
ctggctggtt tgggtggctc aacctttgtg ggagagggtc gcacctttgc accagctggg    180
gtggtttgcc gtatgaccaa caggctcggc aatacggatc attgtccgac tactggcgtc    240
ggggtgcatt caggcatgcg gacactggaa gaagatcagt ggtggcgccc cggcagttgt    300
cgttggtcct ctggtatatg cgttcgacag ttgatcatct cttctggtga agattgctga    360
```

```
cgctctccgg tctcttgcac tgttgtggtg attgtttggg cgcatgttct attcttctga    420
tctgatcgtt cctactgtcg acggcggatc acag                                454
```

<210> SEQ ID NO 11
<211> LENGTH: 803
<212> TYPE: DNA
<213> ORGANISM: Porphyra yezoensis Ueda
<220> FEATURE:
<221> NAME/KEY: misc_feature
<223> OTHER INFORMATION: Terminator region of A2 gene
<220> FEATURE:
<221> NAME/KEY: misc_feature
<222> LOCATION: (780)..(781)
<223> OTHER INFORMATION: n is a, c, g, or t

<400> SEQUENCE: 11

```
gaaaaaaaca ttgctttcgt acgccactgg tcaacatgga tattgaacga ggacggtgaa     60
gactccgtgg ggcgccagga atgcgtgatc agactttctt gacagcttag ctgctttgca    120 agagggcgc ccatcctgcc ccagagccgg tcaagagact taccgctggc gccgcgcatg     180
accagcagcg acgcgttaag acgaggacac gtccagccac atggacaaga aacaaaaaaa    240
acaaaaccaa gaaacgtttg ggcaactgga caaaaacgtg gccacagcag tccaagatga    300
tcgctccgca acagacgtcc atcgcggcaa tcttgccgga gcggccaccc caaacgtgcc    360
atgagaaaca aatcaccacc acaaaaaaga gaattccaac agagcctgac catcgacacg    420
cggggggggg ggcagcaacg cgctcgttcc cggggctca cccccgccca ctgactccag     480
cacggagccc gtgggccaac cactacctgc gcagcggctg gaatgggggg tccatgttca    540
cgcacaggcc ctggccaaga cccagctcca tcattggcaa agccagcccc aagtcaaggt    600
cgacgtcggc gttcgcgttc gcgtctgcgt cggcgtcagc atcagcgtcc gaattgtcag    660
ccatgccggc cctgccccc gtagtccacat cacgaatgct cgtcgggctg tgcccacccc     720
actgtgcgct gctctctccg gattcatccc gtgtccatga cgctgcctcc attcgaggan    780
nagactgtcg ccagcaacac cgg                                            803
```

<210> SEQ ID NO 12
<211> LENGTH: 27
<212> TYPE: DNA
<213> ORGANISM: Artificial
<220> FEATURE:
<223> OTHER INFORMATION: Primer EF47X2

<400> SEQUENCE: 12

```
ggtctagaaa gacgggtacg atagcga                                         27
```

<210> SEQ ID NO 13
<211> LENGTH: 28
<212> TYPE: DNA
<213> ORGANISM: Artificial
<220> FEATURE:
<223> OTHER INFORMATION: Primer EF47X

<400> SEQUENCE: 13

```
cctctagact tctccttccc catgatga                                        28
```